(12) United States Patent
Reyes et al.

(10) Patent No.: US 6,335,184 B1
(45) Date of Patent: *Jan. 1, 2002

(54) LINKED LINEAR AMPLIFICATION OF NUCLEIC ACIDS

(75) Inventors: Antonio Arevalo Reyes, Danville; Robert Bruce Wallace, Greenbrae; Luis A. Ugozzoli, San Rafael, all of CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/228,324

(22) Filed: Jan. 11, 1999

Related U.S. Application Data

(63) Continuation-in-part of application No. 08/826,532, filed on Apr. 2, 1997, now Pat. No. 6,027,923, which is a continuation-in-part of application No. 08/095,442, filed on Jul. 23, 1993, now abandoned.

(51) Int. Cl.⁷ .................................................. C12P 19/34
(52) U.S. Cl. .......................................... 435/91.2; 435/6
(58) Field of Search ..................................... 435/6, 91.2

(56) References Cited

FOREIGN PATENT DOCUMENTS

| | | |
|---|---|---|
| EP | 0332435 A | 9/1989 |
| EP | 0416817 A | 3/1991 |
| WO | WO9421820 A | 9/1994 |
| WO | WO9503432 A | 2/1995 |

OTHER PUBLICATIONS

Brow et al., PCR Protocols, Ed. by Innis et al., p. 189–96, 1990.*

* cited by examiner

*Primary Examiner*—Scott W. Houtteman
(74) *Attorney, Agent, or Firm*—Birch, Stewart, Kolasch & Birch, LLP

(57) ABSTRACT

The extensive synthesis ("amplification") of a nucleic acid sequence of interest is attained through a linked series of multi-cycle primer extension reactions (LLA). The primers used in each of the primer extension reactions of the process contain non-replicable and/or cleavable elements that halt nucleic acid synthesis and thereby prevent the synthesized molecules from serving as templates in subsequent cycles. Synthesized molecules accumulate during primer extension in a mathematically linear fashion, thereby rendering the process relatively insensitive to contaminating nucleic acids. Multiple primer sets are employed, and simultaneously included in the reaction mixture, thereby ensuring the accumulation of a large number of copies of the nucleic acid sequence of interest. The invention also provides for the detection of an amplified nucleic acid sequence of interest, as well as reagent kits for carrying out the reaction.

11 Claims, 16 Drawing Sheets

(e)

(g)

FIG.6
(d)
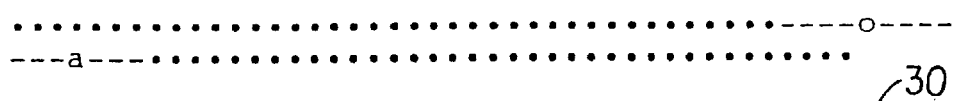
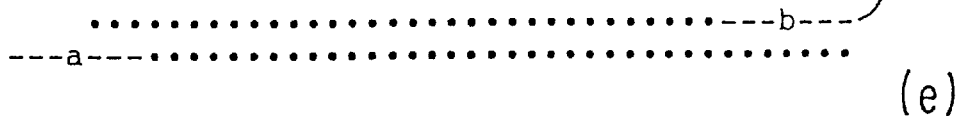
(e)
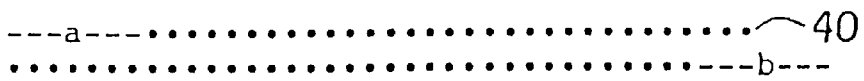
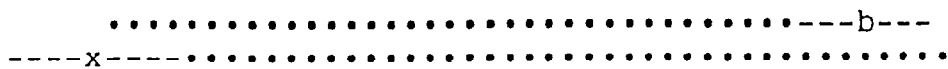

FIG. 9A

REACTION 3A

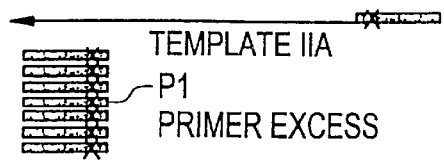

TEMPLATE IIA
P1
PRIMER EXCESS

↓ o CYCLES OF DENATURATION, ANNEALING AND PRIMER EXTENSION

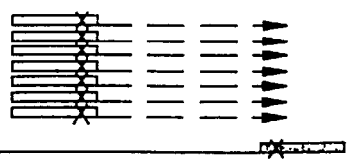

IIIA o COPIES

FIG. 9B

REACTION 4A

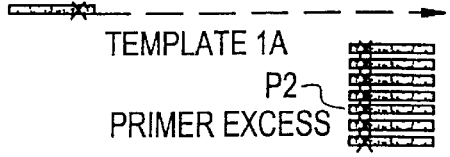

TEMPLATE 1A
P2
PRIMER EXCESS

↓ p CYCLES OF DENATURATION, ANNEALING AND PRIMER EXTENSION

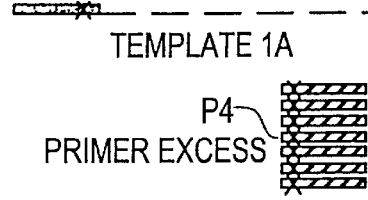

IVA p COPIES

FIG. 9C

REACTION 3B

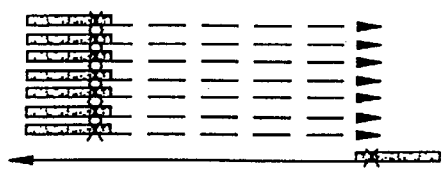

TEMPLATE IIA
P3
PRIMER EXCESS

↓ o' CYCLES OF DENATURATION, ANNEALING AND PRIMER EXTENSION

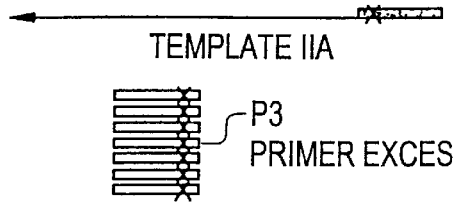

IIIB o' COPIES

FIG. 9D

REACTION 4B

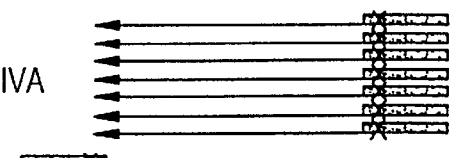

TEMPLATE 1A
P4
PRIMER EXCESS

↓ p' CYCLES OF DENATURATION, ANNEALING AND PRIMER EXTENSION

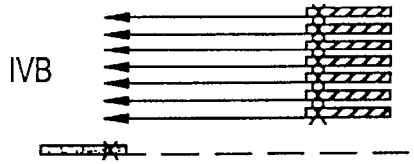

IVB p' COPIES

REACTION 5

REACTION 6

FIG. 11
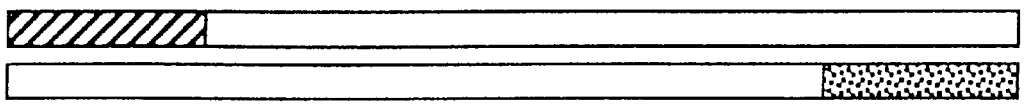
- PRODUCT OF A PCR REACTION IS COMPLETELY DOUBLE STRANDED
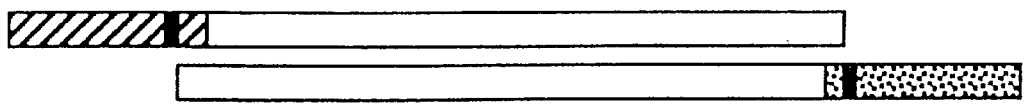
- PRODUCTS OF AN LLA REACTION CAN BE ANNEALED TO FORM A DUPLEX WITH SINGLE STRANDED ENDS
- THIS PRODUCT IS SHORTER THAN THE CORRESPONDING PCR FRAGMENT
▌ Non-replicable element

FIG. 12

```
CCTCACCCTGTGGAGCCACACCCTAGGGTTGGCCAATCTACTCCCAGGAGCAGGAGCCAGGGCTGGGCATAAAAGTCAGGGCAGAG  95
                    |——— bgp-5 35 ———▶|                              |——— bgp-1 22 ———▶|

CCATCTATTGCTTACATTTGCTTCTGACACAACTGTGTTCACTAGCAAACCTCAAACAGACACCATGGTGCACCTGACTCCTGAGGAGAAGTCTGC  190

CGTTACTGCCCTGTGGGGCAAGGTGAACGTGGATGAAGTTGGTGGTGAGGCCCTGGGCAGGTTGGTATCAAGGTTACAAGACAGGTTTAAGGAGA  285

CCAATAGAAACTGGGCATGTGGAGACAGAGAAGACTCTTGGGTTTCTGATAGGCACTGACTCTCTCTGCCTATTGGTCTATTTTCCCACCCTTAG  380
                                                                 |——— bgp-2 22 ———▶|
                                                                              ▼

GCTGCTGGTGGTCTACCCTTGGACCCAGAGGTTCTTTGAGTCCCTTTGG ▲ 428
         |——— bgp-4 35 ———▶|
                        ▼
```

FIG. 13

5'- TTCCCAACCATTCCCTTATCCAGGCTTTTTGACAACGCTAGTCTCCGGCCCATCGTCTCTGCACCAGCTGGCC

———GH1——— ———Md114———

TTTGACACCTACCAGGAGTTGTAAGCTCTCTTGGGGAATGGGTGCGCATCAGGGGTGGCAGGAAGGGGTGACT

TTCCCCCGCTGGGAAATAAGAGGAGACTAAGGAGCTCAGGGTTTTTCCCGAAGCGAAAATGCAGGCAGA

TGAGCACACGCTGAGTGAGGTCCCCAGAAAGTAACAATGGGAGCTGGTCTCCCAGCGTAGACCTTGGTGGGC

GGTCCTTCTCCTAGGAAGAAGCCTATATCCCAAAGGAACAGAAGTATTCATTCCTGCAAACCCCCAGACCT

CCCTCTGTTTCTCAGAGTCTATTCCGACACCCTCCAACAGGGAGGAAACACAACAGAAATCC -3'

———GH2———

```
                         SEQUENCE LISTING

<160> NUMBER OF SEQ ID NOS: 64

<210> SEQ ID NO 1
<211> LENGTH: 428
<212> TYPE: DNA
<213> ORGANISM: Homo sapiens

<400> SEQUENCE: 1
cctcaccctg tggagccaca ccctagggtt ggccaatcta ctcccaggag cagggagggc     60
aggagccagg gctgggcata aaagtcaggg cagagccatc tattgcttac atttgcttct    120
gacacaactg tgttcactag caacctcaaa cagacaccat ggtgcacctg actcctgagg    180
agaagtctgc cgttactgcc ctgtgggca aggtgaacgt ggatgaagtt ggtggtgagg     240
ccctgggcag gttggtatca aggttacaag acaggtttaa ggagaccaat agaaactggg    300
catgtggaga cagagaagac tcttgggttt ctgataggca ctgactctct ctgcctattg    360
gtctattttc ccaccttag gctgctggtg gtctacctt ggaccagag gttctttgag      420 tcctttgg                                                            428

<210> SEQ ID NO 2
<211> LENGTH: 30
<212> TYPE: DNA
<213> ORGANISM: Homo sapiens

<400> SEQUENCE: 2
gctcccttag catgggagag tctccggttc                                     30

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (1)
<223> OTHER INFORMATION: gctccctta-"non-replicable element"

<400> SEQUENCE: 3
catgggagag tctccggttc                                                20

<210> SEQ ID NO 4
<211> LENGTH: 12
<212> TYPE: DNA
<213> ORGANISM: Homo sapiens

<400> SEQUENCE: 4
gaaccggaga ct                                                        12

<210> SEQ ID NO 5
<211> LENGTH: 22
<212> TYPE: DNA
<213> ORGANISM: Homo sapiens

<400> SEQUENCE: 5
```

```
gggtgggaaa atagaccaat ag                                              22

<210> SEQ ID NO 6
<211> LENGTH: 17
<212> TYPE: DNA
<213> ORGANISM: Homo sapiens
<220> FEATURE:
<221> NAME/KEY: misc_feature
<222> LOCATION: (17)
<223> OTHER INFORMATION: "non-replicable element"-atag

<400> SEQUENCE: 6
gggtgggaaa atagacc                                                    17

<210> SEQ ID NO 7
<211> LENGTH: 30
<212> TYPE: DNA
<213> ORGANISM: Homo sapiens

<400> SEQUENCE: 7
ggcaggagcc agggctgggc ataaaagtca                                      30

<210> SEQ ID NO 8
<211> LENGTH: 25
<212> TYPE: DNA
<213> ORGANISM: Homo sapiens
<220> FEATURE:
<221> NAME/KEY: misc_feature
<222> LOCATION: (25)
<223> OTHER INFORMATION: "non-replicable element"-gtca

<400> SEQUENCE: 8
ggcaggagcc agggctgggg ataaa                                           25

<210> SEQ ID NO 9
<211> LENGTH: 24
<212> TYPE: DNA
<213> ORGANISM: Homo sapiens

<400> SEQUENCE: 9
ctgcagtaac ggcagacttc tcct                                            24

<210> SEQ ID NO 10
<211> LENGTH: 30
<212> TYPE: DNA
<213> ORGANISM: Homo sapiens
<220> FEATURE:
<221> NAME/KEY: misc_feature
<222> LOCATION: (30)
<223> OTHER INFORMATION: "non-replicable element"-catc

<400> SEQUENCE: 10
ccagggctgg gcataaaagt cagggcagag                                      30

<210> SEQ ID NO 11
<211> LENGTH: 30
<212> TYPE: DNA
<213> ORGANISM: Homo sapiens
<220> FEATURE:
<221> NAME/KEY: misc_feature
<222> LOCATION: (30)
<223> OTHER INFORMATION: "non-replicable feature"-gtca

<400> SEQUENCE: 11
gggtgggaaa atagaccaat aggcagagag                                      30
```

```
<210> SEQ ID NO 12
<211> LENGTH: 17
<212> TYPE: DNA
<213> ORGANISM: Homo sapiens
<220> FEATURE:
<221> NAME/KEY: misc_feature
<222> LOCATION: (17)
<223> OTHER INFORMATION: "non-replicable element"-ctct

<400> SEQUENCE: 12
ccaaaggact caaagaa                                                     17

<210> SEQ ID NO 13
<211> LENGTH: 17
<212> TYPE: DNA
<213> ORGANISM: Homo sapiens
<220> FEATURE:
<221> NAME/KEY: misc_feature
<222> LOCATION: (17)
<223> OTHER INFORMATION: "non-replicable element"-cacc

<400> SEQUENCE: 13
cctcagcgtg tggagcc                                                     17

<210> SEQ ID NO 14
<211> LENGTH: 22
<212> TYPE: DNA
<213> ORGANISM: Homo sapiens

<400> SEQUENCE: 14
caggagtcag gtgcaccatg gt                                               22

<210> SEQ ID NO 15
<211> LENGTH: 422
<212> TYPE: DNA
<213> ORGANISM: Homo sapiens

<400> SEQUENCE: 15
ttcccaacca ttcccttatc caggcttttt gacaacgcta gtctccgcgc ccatcgtctg      60
caccagctgg cctttgacac ctaccaggag tttgtaagct cttggggaat gggtgcgcat     120 cagggggtggc aggaaggggt gactttcccc cgctgggaaa taagaggagg agactaagga    180
gctcagggtt tttcccgaag cgaaaatgca ggcagatgag cacacgctga gtgaggttcc     240
cagaaaagta acaatgggag ctggtctcca gcgtagacct tggtgggcgg tccttctcct     300
aggaagaagc ctatatccca aaggaacaga agtattcatt cctgcagaac ccccagacct     360
ccctctgttt ctcagagtct attccgacac cctccaacag ggaggaaaca caacagaaat     420
cc                                                                   422

<210> SEQ ID NO 16
<211> LENGTH: 18
<212> TYPE: DNA
<213> ORGANISM: Homo sapiens
<220> FEATURE:
<223> OTHER INFORMATION: Description of Combined DNA/RNA
      Molecule:synthesized primer

<400> SEQUENCE: 16
ttcccaacca utccctta                                                    18

<210> SEQ ID NO 17
<211> LENGTH: 18
<212> TYPE: DNA
<213> ORGANISM: Homo sapiens
```

<220> FEATURE:
<223> OTHER INFORMATION: Description of Combined DNA/RNA
      Molecule:synthesized primer

<400> SEQUENCE: 17
ggatttctgu tgtgtttc                                                      18

<210> SEQ ID NO 18
<211> LENGTH: 18
<212> TYPE: DNA
<213> ORGANISM: Homo sapiens

<400> SEQUENCE: 18
ttcccaacca ttccctta                                                      18

<210> SEQ ID NO 19
<211> LENGTH: 18
<212> TYPE: DNA
<213> ORGANISM: Homo sapiens

<400> SEQUENCE: 19
ggatttctgt tgtgtttc                                                      18

<210> SEQ ID NO 20
<211> LENGTH: 18
<212> TYPE: DNA
<213> ORGANISM: Homo sapiens

<400> SEQUENCE: 20
tagcgttgtc aaaaagcc                                                      18

<210> SEQ ID NO 21
<211> LENGTH: 23
<212> TYPE: DNA
<213> ORGANISM: Homo sapiens
<220> FEATURE:
<221> NAME/KEY: misc_feature
<222> LOCATION: (23)
<223> OTHER INFORMATION: "non-replicable element"-gac

<400> SEQUENCE: 21
taagccagtg ccagaagagc caa                                                23

<210> SEQ ID NO 22
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-tca

<400> SEQUENCE: 22
tacggctgtc atcacttaga c                                                  21

<210> SEQ ID NO 23
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-gtt

<400> SEQUENCE: 23
ccctgtggag ccacaccta g                                                   21

```
<210> SEQ ID NO 24
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ggg

<400> SEQUENCE: 24
aatctactcc caggagcagg g                                              21

<210> SEQ ID NO 25
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-tca

<400> SEQUENCE: 25
gagccagggc tgggcataaa a                                              21

<210> SEQ ID NO 26
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-att

<400> SEQUENCE: 26
ggcagagcca tctattgctt a                                              21

<210> SEQ ID NO 27
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-act

<400> SEQUENCE: 27
tgcttctgac acaactgtgt t                                              21

<210> SEQ ID NO 28
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ggt

<400> SEQUENCE: 28
agcaacctca aacagacacc a                                              21

<210> SEQ ID NO 29
<211> LENGTH: 21
<212> TYPE: DNA
<213> ORGANISM: Homo sapiens
<220> FEATURE:
<221> NAME/KEY: misc_feature
<222> LOCATION: (21)
```

<223> OTHER INFORMATION: "non-replicable element"-gtt

<400> SEQUENCE: 29
cctcaccacc aacttcatcc a                                         21

<210> SEQ ID NO 30
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ggg

<400> SEQUENCE: 30
aaccttgata ccaacctgcc c                                         21

<210> SEQ ID NO 31
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ttg

<400> SEQUENCE: 31
tattggtctc cttaaacctg t                                         21

<210> SEQ ID NO 32
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ttt

<400> SEQUENCE: 32
ttctctgtct ccacatgccc a                                         21

<210> SEQ ID NO 33
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-gag

<400> SEQUENCE: 33
cagtgcctat cagaaaccca a                                         21

<210> SEQ ID NO 34
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-agt

<400> SEQUENCE: 34
aaatagacca ataggcagag a                                         21

<210> SEQ ID NO 35
<211> LENGTH: 21

```
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-gga

<400> SEQUENCE: 35
gaccaccagc agcctaaggg t                                              21

<210> SEQ ID NO 36
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ata

<400> SEQUENCE: 36
ttcctatgac atgaacttaa c                                              21

<210> SEQ ID NO 37
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ccc

<400> SEQUENCE: 37
aaactgtacc ctgttacttc t                                              21

<210> SEQ ID NO 38
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-tct

<400> SEQUENCE: 38
caatcattcg tctgtttccc a                                              21

<210> SEQ ID NO 39
<211> LENGTH: 27
<212> TYPE: DNA
<213> ORGANISM: Homo sapiens

<400> SEQUENCE: 39
taagccagtg ccagaagagc caaggac                                        27

<210> SEQ ID NO 40
<211> LENGTH: 25
<212> TYPE: DNA
<213> ORGANISM: Homo sapiens

<400> SEQUENCE: 40
gaccaccagc agcctaaggg tggga                                          25

<210> SEQ ID NO 41
<211> LENGTH: 24
<212> TYPE: DNA
<213> ORGANISM: Homo sapiens
```

-continued

```
<400> SEQUENCE: 41
catcattcgt ctgtttccca ttct                                          24

<210> SEQ ID NO 42
<211> LENGTH: 25
<212> TYPE: DNA
<213> ORGANISM: Homo sapiens

<400> SEQUENCE: 42
caccttgccc cacagggcag taacg                                         25

<210> SEQ ID NO 43
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-ata

<400> SEQUENCE: 43
agcacaccaa catgacacat g                                             21

<210> SEQ ID NO 44
<211> LENGTH: 23
<212> TYPE: DNA
<213> ORGANISM: Homo sapiens
<220> FEATURE:
<221> NAME/KEY: misc_feature
<222> LOCATION: (23)
<223> OTHER INFORMATION: "non-replicable element"-ata

<400> SEQUENCE: 44
cacatgtacc ctagaactta aag                                           23

<210> SEQ ID NO 45
<211> LENGTH: 19
<212> TYPE: DNA
<213> ORGANISM: Homo sapiens
<220> FEATURE:
<221> NAME/KEY: misc_feature
<222> LOCATION: (19)
<223> OTHER INFORMATION: "non-replicable element"-tat

<400> SEQUENCE: 45
aattggttcc agcgaaagc                                                19

<210> SEQ ID NO 46
<211> LENGTH: 19
<212> TYPE: DNA
<213> ORGANISM: Homo sapiens
<220> FEATURE:
<221> NAME/KEY: misc_feature
<222> LOCATION: (19)
<223> OTHER INFORMATION: "non-replicable element"-atc

<400> SEQUENCE: 46
caggcaggaa caacaccat                                                19

<210> SEQ ID NO 47
<211> LENGTH: 19
<212> TYPE: DNA
<213> ORGANISM: Homo sapiens
<220> FEATURE:
<221> NAME/KEY: misc_feature
<222> LOCATION: (19)
<223> OTHER INFORMATION: "non-replicable element"-aac
```

<400> SEQUENCE: 47
agagcagttc aaccagggg                                                        19

<210> SEQ ID NO 48
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-aga

<400> SEQUENCE: 48
tcttagagtt tgatgaaccc a                                                     21

<210> SEQ ID NO 49
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-aga

<400> SEQUENCE: 49
aaatgatgcc cagtgcttaa c                                                     21

<210> SEQ ID NO 50
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-tca

<400> SEQUENCE: 50
ccatactaca gtgacgtgga c                                                     21

<210> SEQ ID NO 51
<211> LENGTH: 19
<212> TYPE: DNA
<213> ORGANISM: Homo sapiens
<220> FEATURE:
<221> NAME/KEY: misc_feature
<222> LOCATION: (19)
<223> OTHER INFORMATION: "non-replicable element"-taa

<400> SEQUENCE: 51
gagagacatc gcctctggg                                                        19

<210> SEQ ID NO 52
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-gaa

<400> SEQUENCE: 52
ttctagccag aagaaattct c                                                     21

<210> SEQ ID NO 53
<211> LENGTH: 21
<212> TYPE: DNA

<213> ORGANISM: Homo sapiens
<220> FEATURE:
<221> NAME/KEY: misc_feature
<222> LOCATION: (21)
<223> OTHER INFORMATION: "non-replicable element"-atg

<400> SEQUENCE: 53
ttatttagcc aggagaccta a                                         21

<210> SEQ ID NO 54
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-cca

<400> SEQUENCE: 54
ctgttctctt gaaggaaatg c                                         21

<210> SEQ ID NO 55
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-caa

<400> SEQUENCE: 55
ggtgctaaaa aggactactt g                                         21

<210> SEQ ID NO 56
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-aaa

<400> SEQUENCE: 56
cttcggcagt gatggtactg a                                         21

<210> SEQ ID NO 57
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-aag

<400> SEQUENCE: 57
aacagacctg gaatttgaaa c                                         21

<210> SEQ ID NO 58
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-acc

<400> SEQUENCE: 58
caacttgctc aacacatcca a                                         21

-continued

```
<210> SEQ ID NO 59
<211> LENGTH: 21
<212> TYPE: DNA
<213> ORGANISM: Homo sapiens
<220> FEATURE:
<221> NAME/KEY: misc_feature
<222> LOCATION: (21)
<223> OTHER INFORMATION: "non-replicable element"-aat

<400> SEQUENCE: 59
aaggaagaaa ttaggaaagg c                                          21

<210> SEQ ID NO 60
<211> LENGTH: 22
<212> TYPE: DNA
<213> ORGANISM: Homo sapiens
<220> FEATURE:
<221> NAME/KEY: misc_feature
<222> LOCATION: (22)
<223> OTHER INFORMATION: "non-replicable element"-att

<400> SEQUENCE: 60
catttttagg agggttatta cc                                         22

<210> SEQ ID NO 61
<211> LENGTH: 24
<212> TYPE: DNA
<213> ORGANISM: Homo sapiens

<400> SEQUENCE: 61
ctacttctaa tctgtaagag caga                                       24

<210> SEQ ID NO 62
<211> LENGTH: 22
<212> TYPE: DNA
<213> ORGANISM: Homo sapiens

<400> SEQUENCE: 62
gaaaggttac ttcaaggaca aa                                         22

<210> SEQ ID NO 63
<211> LENGTH: 22
<212> TYPE: DNA
<213> ORGANISM: Homo sapiens
<220> FEATURE:
<221> NAME/KEY: misc_feature
<222> LOCATION: (22)
<223> OTHER INFORMATION: "non-replicable element"-gga

<400> SEQUENCE: 63
ctaatctgta agagcagatc cc                                         22

<210> SEQ ID NO 64
<211> LENGTH: 22
<212> TYPE: DNA
<213> ORGANISM: Homo sapiens
<220> FEATURE:
<221> NAME/KEY: misc_feature
<222> LOCATION: (22)
<223> OTHER INFORMATION: "non-replicable element"-aaa

<400> SEQUENCE: 64
ttctgaaagg ttacttcaag ga                                         22
```

LINKED LINEAR AMPLIFICATION OF NUCLEIC ACIDS

CROSS REFERENCE TO RELATED APPLICATION

This application is a continuation-in-part of application Ser. No. 08/826,532, filed Apr. 2, 1997, now U.S. Pat. No. 6,027,923, which is a continuation-in-part of application Ser. No. 08/095,442, filed Jul. 23, 1993, now abandoned, both of which are hereby incorporated by reference.

BACKGROUND OF THE INVENTION

1. Technical Field

The present invention relates to the in vitro replication of nucleic acids. More specifically, the invention relates to a process for replicating a nucleic acid sequence of interest, with large quantities of the desired sequence ultimately resulting from the linkage of primer extension reactions wherein the sequence of interest accumulates in a mathematically linear fashion.

2. Brief Description of the Background Art

The extensive replication of nucleic acids, today known as (and referred to herein as) nucleic acid "amplification," finds wide utility, both practical and theoretical, in a variety of contexts. H. G. Khorana and his co-workers first proposed the use of an in vitro DNA amplification process to increase available amounts of double-stranded DNA (partial sequences of the gene for the major yeast alanine t-RNA) that had been created by the enzymatic ligation of synthetic DNA's. See K. Kleppe et al.; J. Mol. Biol. 56:341–361 (1971). Later, in vitro amplification was applied to the amplification of genomic DNA (Saiki et al., Science 230:1350–1354 (1985)) as the technique now known as the polymerase chain reaction or "PCR." Through the wide availability of synthetic oligonucleotide primers, thermostable DNA polymerases and automated temperature cycling apparatus, PCR became a widely-utilized tool of the molecular biologist.

The PCR process is referred to in the literature as an "exponential amplification" process. In each round or "cycle" of primer extension, a primer binding site for the other primer is synthesized. Thus, each of the synthetic DNA molecules produced in any of the previous cycles is available to serve as a template for primer-dependent replication. This aspect of the process, coupled with the presence of a sufficiently large number of primer molecules, results in synthetic DNA accumulating in a mathematically exponential manner as the reaction proceeds.

Although PCR has proven to be a valuable technique for the molecular biologist, and has been used extensively in the fields of human genetic research, diagnostics and forensic science, and even in the detection of antibodies, disadvantages nevertheless have been recognized. The PCR process can be difficult to quantify accurately, mainly because the amplification products increase exponentially with each round of amplification. The products of PCR, namely, double-stranded DNA molecules, are difficult to analyze or sequence per se. Strand separation typically must be carried out prior to sequencing or other downstream processes that require single stranded nucleic acids, such as hybridization to a probe capable of detecting the sequence of interest.

The PCR process also has proven to be quite susceptible to contamination generated through the transfer of previously amplified DNA sequences into a new reaction. This problem appears to be caused by the facts that (1) very large amounts of DNA are generated in any given reaction cycle and (2) the process uses all product DNA strands as templates in subsequent cycles. Even minute quantities of contaminating DNA can be exponentially amplified and lead to erroneous results. See Kwok and Higuchi, Nature 339:237–238 (1989). Various methods to reduce such contamination have been reported in the literature (e.g. chemical decontamination, physical treatment, enzyme treatment and utilizing closed systems), as these contamination problems are widely recognized. See, John B. Findlay, "Development of PCR for in vitro Diagnostics," presented at "Genetic Recognition," Nov. 20, 1992, San Diego, Calif.

There has remained a need for new nucleic acid (DNA) amplification methods that provide large amounts of DNA, and that selectively amplify only a specific sequence of interest, but which avoid the problems now associated with the "PCR" reaction. Specifically, there has remained a need for nucleic acid amplification methods that ultimately produce large amounts of a nucleic acid molecule of interest, or large amounts of a molecule containing a nucleic acid sequence of interest, but are relatively insensitive to the presence of contaminating nucleic acids. There has also remained a need for nucleic acid amplification methods that generate single-stranded products.

SUMMARY OF THE INVENTION

The foregoing and other needs are met by the present invention, which in one aspect provides a process for amplifying a specific nucleic acid sequence of interest within complementary nucleic acid strands contained in a sample, the process including the steps of:

(a) contacting the strands with a primer that contains a non-replicable element, under conditions such that first generation primer extension products are synthesized using said strands as templates, and wherein the primer for a strand is selected such that a first generation primer extension product synthesized thereon, when separated from the strand, can serve as a template for synthesis of a second generation primer extension product of the primer for the complement of the strand;

(b) separating the first generation primer extension products from their templates to produce single-stranded molecules; and (c) treating the first generation primer extension products with the primers of step (a) under conditions such that second generation primer extension products are synthesized using the first generation primer extension products as templates; wherein the second generation primer extension products contain at least a portion of the nucleic acid sequence of interest and cannot serve as templates for the synthesis of extension products of the primers which were extended to synthesize their templates.

In other aspects of the invention, the products of step (c) are separated to produce single-stranded molecules, and the entire process is repeated at least once. Step (c) preferably is repeated many times, with the process being carried out in an automated fashion under the control of a programmable thermal cycling apparatus.

Following the accumulation of second generation primer extension products, each of which is incapable of serving as a template for the primer extended to prepare its first generation template, a new set of primers that contain non-replicable elements can be employed. The new set of primers advantageously bind to the second generation synthetic products, bounding the sequence of interest to be amplified. The linear replication process is again carried out through a number of cycles. Such "linking together" of multi-cycle primer extension reactions ultimately results in thousand-fold or million- fold amplification of the original nucleic acid sequence of interest. Thus, the present process is deemed "linked linear amplification" or "LLA."

In another aspect of the invention, multiple (nested) sets of primers containing non-replicable elements can be provided in a single amplification reaction mixture. The sets are selected so as to be capable of binding to their respective templates under decreasingly stringent conditions. Alternatively, as in Examples 8–11, the LLA reaction can be performed using a nested set of primers under a single stringency condition under which all of the primers in the set are capable of simultaneously binding to their respective complementary sites. Thus, all the components necessary to carry out several linked linear amplifications can be provided in a single reaction mixture.

In yet another aspect of the invention, allele- specific nucleic acid replication is carried out according to the present invention with the use of primers directed to specific polymorphic sites on the template that are known to be indicative of a genetic disease or disorder, such as sickle cell disease. The allele-specific primers, containing non-replicable elements, are designed so that they prime nucleic acid synthesis of only those templates containing the desired allele.

The synthetic nucleic acid molecules resulting from the present process can be used in the diagnosis of genetic disorders or diseases, as reagents in further techniques such as gene cloning, for forensic identification, etc.

The process described herein also can be carried out using a single nucleic acid strand as a starting material. Such a process comprises:

(a) contacting the strand with a first primer containing a non-replicable element, under conditions such that a first generation primer extension product is synthesized using the strand as a template;

(b) separating the first generation primer extension product from its template to produce single stranded molecules; and (c) contacting the first generation primer extension product with a second primer containing a non-replicable element under conditions such that a second generation primer extension product is synthesized using the first generation primer extension product as a template;

wherein the primers are selected so that the second generation primer extension product cannot serve as a template for extension of the first primer. Steps (a)–(c) can be repeated many times, resulting in extensive nucleic acid synthesis, following which the reaction is linked to a subsequent reaction using a new set of primers.

The processes described herein also can be carried out using primers containing cleavable elements. This process comprises:

(a) contacting the strands of a nucleic acid template with a first primer containing a cleavable element, under conditions such that a first generation primer extension product is synthesized using the strand as a template;

(b) separating the first generation primer extension product from its template to produce single stranded molecules;

(c) treating the single stranded molecules such that the first generation primer extension product is cleaved at the position of the cleavable element;

(d) contacting the first generation primer extension product with a second primer under conditions such that a second generation primer extension product is synthesized using the first generation primer extension product as a template;

wherein the primers are selected so that the second generation primer extension product cannot serve as a template for extension of the first primer, when the first primer extension product has been cleaved at the cleavable element. Steps (a)–(d) can be repeated many times, resulting in extensive nucleic acid synthesis, following which the reaction may be linked to a subsequent reaction using a new set of primers. Additionally, the second primer may optionally contain a cleavable element such that the linked linear amplification reaction can be carried out on either a double-stranded or a single-stranded starting template.

Furthermore, the process described herein can be carried by simultaneously combining a series of nested primers. Such a process comprises complementary first and second nucleic acid strands, comprising:

(a) combining the strands of a nucleic acid template in a reaction mixture with a series of nested primers, each primer containing a non-replicable element and/or a cleavable element, the series of nested primers comprising a plurality of primers which are complementary to different portions of said strands and the nested primers flank the sequence of interest but do not overlap with one another at the position of the non-replicable element or cleavable element;

(b) subjecting the reaction mixture to conditions such that first generation primer extension products are produced from first primers, and not from other of the series of nested primers using the first and second strands as templates, wherein the first primers are primers of said nested primers which are most 3' with respect to the sequence of interest, and wherein the first primers are selected such that a first generation primer extension product from this step, when separated from its template, can serve as a template for synthesis of a second generation extension product of the first primer for the complement of the strand;

(c) separating the first generation primer extension products from their respective templates to produce single-stranded molecules;

(d) exposing the reaction mixture to conditions such that second generation primer extension products are generated by the first primers using first generation primer extension products as templates, wherein the second generation primer extension products contain at least a portion of the sequence of the nucleic acid sequence of interest and no more than an insufficient portion of the binding site for the first primers for producing the first generation primer extension products;

(e) separating the second generation primer extension products from their template to produce single stranded molecules;

(f) subjecting the reaction mixture of step (e) to reaction conditions such that next generation primer extension products are synthesized from another primer of the series of nested primers using second generation primer extension products as templates, and separating the thus produced next generation primer extension products from their templates to produce single-stranded molecules; and (g) repeating step (f) such that each repeat of the step comprises subjecting the reaction mixture to conditions such that next generation primer extension products are synthesized from a different primer of the series of nested primers using the next prior generation primer extension products as templates.

The process described herein can also be carried by simultaneously combining a series of nested primers with complementary first and second nucleic acid strands under a single stringency condition under which all of the primers in the set are capable of simultaneously binding to their respective complementary sites. This process comprises:

(a) combining the strands of a nucleic acid template in a reaction mixture with a series of nested primers, each primer containing a non-replicable element and/or a cleavable element, the series of nested primers comprising a plurality of primers which are complementary to different portions of said strands and the nested primers flank the sequence of interest but do not overlap with one another at the position of the non-replicable element or cleavable element;

(b) subjecting the reaction mixture to conditions whereby each of said primers is capable of binding to its respective complementary site such that first generation primer extension products are produced;

(c) separating the first generation primer extension products from their respective templates to produce single-stranded molecules; and (d) repeating steps (b) and (c) whereby next generation primer extension products are synthesized from a different primer of the series of nested primers using the next prior generation primer extension products as templates, but no primer extension product can serve as a template for a primer whose complementary site on said strand is farther from (i.e. outside) the sequence of interest with respect to the non-replicable element or cleavable element in that extension product.

The present invention also relates to a reagent kit for use in amplifying a particular nucleic acid sequence. Such kit includes, for example, a DNA polymerase, two or more primers for each sequence to be amplified wherein each of said primers comprises a non-replicable element or incorporates a cleavable element, and, optionally, a control nucleic acid sequence capable of being replicated by the primers and DNA polymerase. The kit also may contain a nucleic acid probe capable of indicating the presence or absence of an amplification product of the particular sequence. Where the kit contains primers incorporating a cleavable element, it may also contain reagents for cleaving the primer at the cleavable element.

BRIEF DESCRIPTION OF THE DRAWINGS

FIGS. 5–6 comprise a schematic representation of a nucleic acid amplification process that has been linked to the process represented by FIGS. 1–4.

FIGS. 8–10 present a detailed schematic representation of a linked linear nucleic acid amplification process carried out with four primers according to the present invention.

FIG. 11 is a schematic representation of nucleic acid molecules prepared by the PCR process and by a process according to the present invention.

FIG. 12 is a schematic representation of the sequence of the human β-globin gene (GenBank locus HUMHBB SEQ ID NO: 1) and of several primers described herein.

FIG. 13 is the sequence of Human Growth Hormone Sequence SEQ ID NO: 15 amplified in Example 7. The relative positions of the oligonucleotides used in the experiment are underlined. Oligonucleotide GH1 hybridizes to the complement of the Human Growth Hormone sequence shown.

DETAILED DESCRIPTION OF THE PREFERRED EMBODIMENTS

Figure 1:
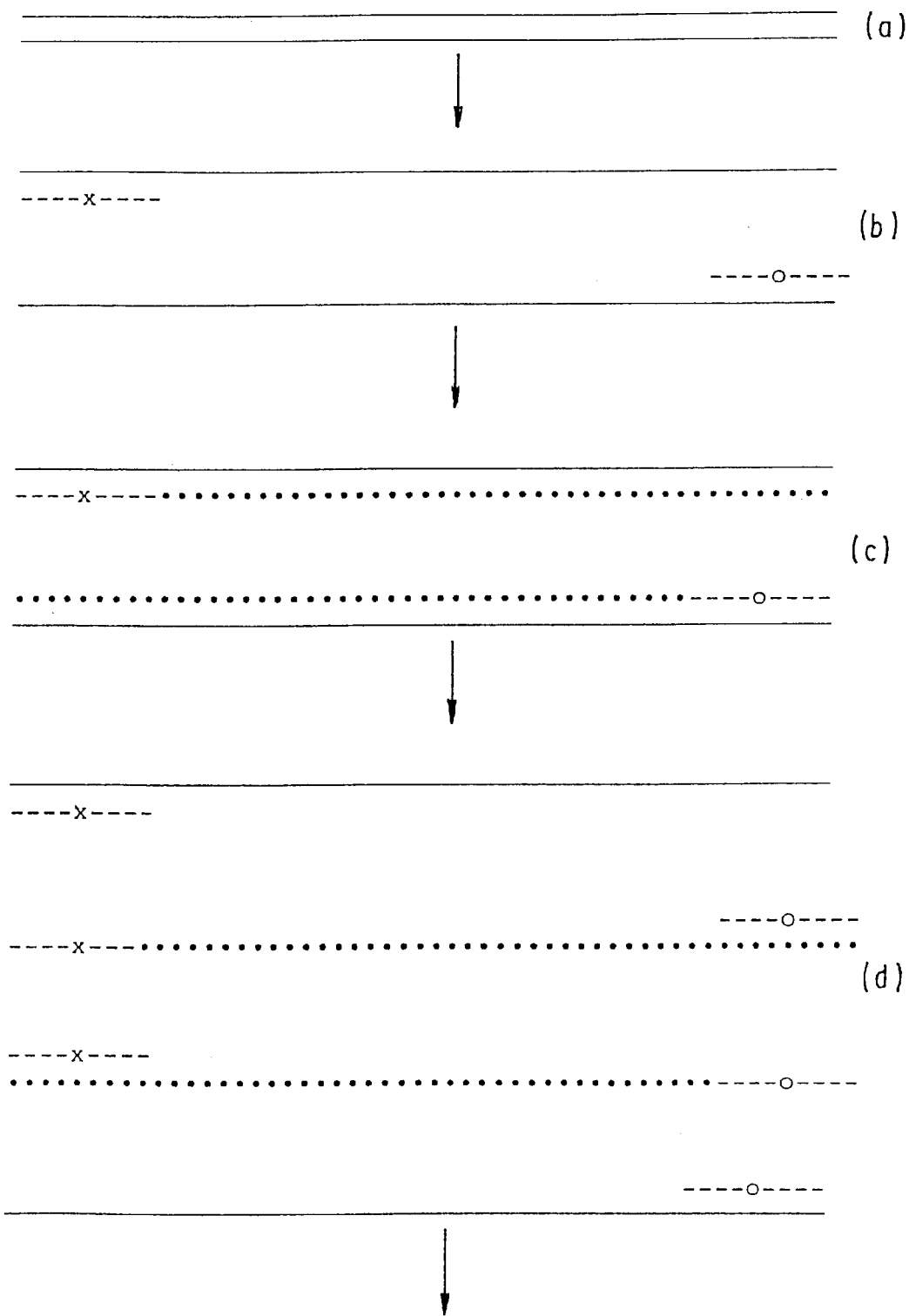
FIGS. 1–4 comprise a schematic representation of a nucleic acid amplification process of the present invention.

The nucleic acid replication process of the present invention is capable of producing large quantities of a specific nucleic acid sequence of interest. The process in its preferred form comprises a linked series of multi-cycle primer extension reactions. In each of the multi-cycle primer extension reactions, primer-dependent nucleic acid replication is carried out through a number of cycles, with the primer extension products accumulating in a numerically linear fashion from cycle to cycle. A unique primer, or set of primers, is provided for each nucleic acid strand in the starting sample that contains the sequence to be amplified. The linear accumulation of primer extension products from cycle to cycle is assured through the use of primers that contain non-replicable elements—elements that halt the primer extension reaction, preventing the nucleic acid polymerase from replicating the entire sequence of the primer. Alternatively, the linear accumulation of the desired primer extension products is assured through the use of primers that contain cleavable elements, where cleavage of the first primer extension product results in a second primer extension product lacking the functional binding site for the first primer. Through the selection of appropriate primers containing such non-replicable or cleavable elements, and appropriate primer annealing conditions, it is ensured that the primer extension products which accumulate in greatest abundance (referred to herein as "second generation primer extension products") cannot serve as templates themselves in subsequent cycles of primer extension using the same primers. Thus, unlike nucleic acid amplification processes (such as "PCR") which utilize the primer extension products from each cycle as templates for subsequent cycles, "exponential amplification" does not occur from cycle to cycle.

The process of the present invention utilizes and takes advantage of a number of important properties of oligonucleotide hybridization and the primer extension reaction. The invention takes advantage of the facts that:

DNA polymerase is able to copy a template DNA many times by sequential cycles of denaturation and primer-dependent elongation.

Primer-dependent elongation can occur, under appropriate conditions, even if the primer is not completely complementary to the template.

Primer extension can utilize a template produced in a previous round of primer extension.

Primer extension is inhibited by abasic sites or by non-nucleotide residues when such are present in the template nucleic acid. Alternatively, primer extension may be inhibited by physically removing a portion of the generation primer extension product by cleaving this molecule at the cleavable sites incorporated into the primers used in the primer extension reaction.

Primer length and composition affect, in known ways, the conditions (e.g., temperature) at which a primer will "prime" polymerase-induced extension on a template.

Primer extension reactions can be performed-in rapid cycles with the aid of thermal cycling apparatus.

The present process advantageously utilizes a series of linear amplification reactions, which can be carried out (linked) either in series or in parallel (i.e., simultaneously) to generated very large number of copies of a nucleic acid sequence of interest. The nucleic acid sequence of interest may encompass essentially the entire length of the template strand(s), or it may comprise only a very minor portion of it. The template strand(s) containing the sequence of interest may be present in a substantially homogeneous sample or as part (even an extremely minor part) of a mixture of nucleic acids.

In accordance with the present invention, a primer that contains a non-replicable or cleavable element is provided for each strand containing a sequence to be amplified. In the case of a double-stranded template, the primer(s) are added either prior to or following denaturation of the template. The primers are permitted to anneal to their respective starting templates, and are extended in the presence of a polymerase enzyme, under conditions appropriate for the function of the enzyme, to form first generation primer extension products. The process is repeated by denaturing the resulting duplexed nucleic acid, permitting the primers to anneal to the strands and again carrying out the primer extension reaction. Primer extension upon the first generation primer extension products yields second generation primer extension products which, due to the presence of non-replicable elements, cannot serve as templates for those same primers in subsequent cycles. Alternatively, where the primer contains a cleavable element, the first generation primer extension products are cleaved at the position of the cleavable element, so that when this first generation primer extension product is annealed to the appropriate primer and extended, the second generation primer extension product formed will lack a binding site for the primer used to generate the first primer extension product.

FIGS. 1–5 present a schematic representation of one series of primer extension reactions (i.e., one linear amplification reaction) carried out on a DNA template according to the process of the present invention. The process is illustrated starting in step (a) with a double-stranded DNA molecule having defined termini The strands of the starting DNA are denoted by solid (—) lines throughout FIGS. 1–4.

The starting duplex is denatured, preferably by heating in a buffer solution containing the same, and the resulting single strands are contacted with a pair of primers (step (b)). Each primer preferably is provided in substantial molar excess of the starting template strand and contains within its sequence a non-replicable or alternatively, a cleavable element, here denoted by (x) or (o) within the primer sequence. Under appropriate conditions, the primers anneal to their respective templates and are elongated (step (c)) according to the primer extension reaction in the presence of a DNA polymerase and the four deoxyribonucleotides. Synthesized DNA is denoted by dotted (●●●●●●) lines in FIGS. 1–4, and the DNA synthesized using the starting duplex DNA as a template is denoted "first generation" DNA. The resulting templates again are denatured, and the primers are annealed (step (d)).

Figure 2:
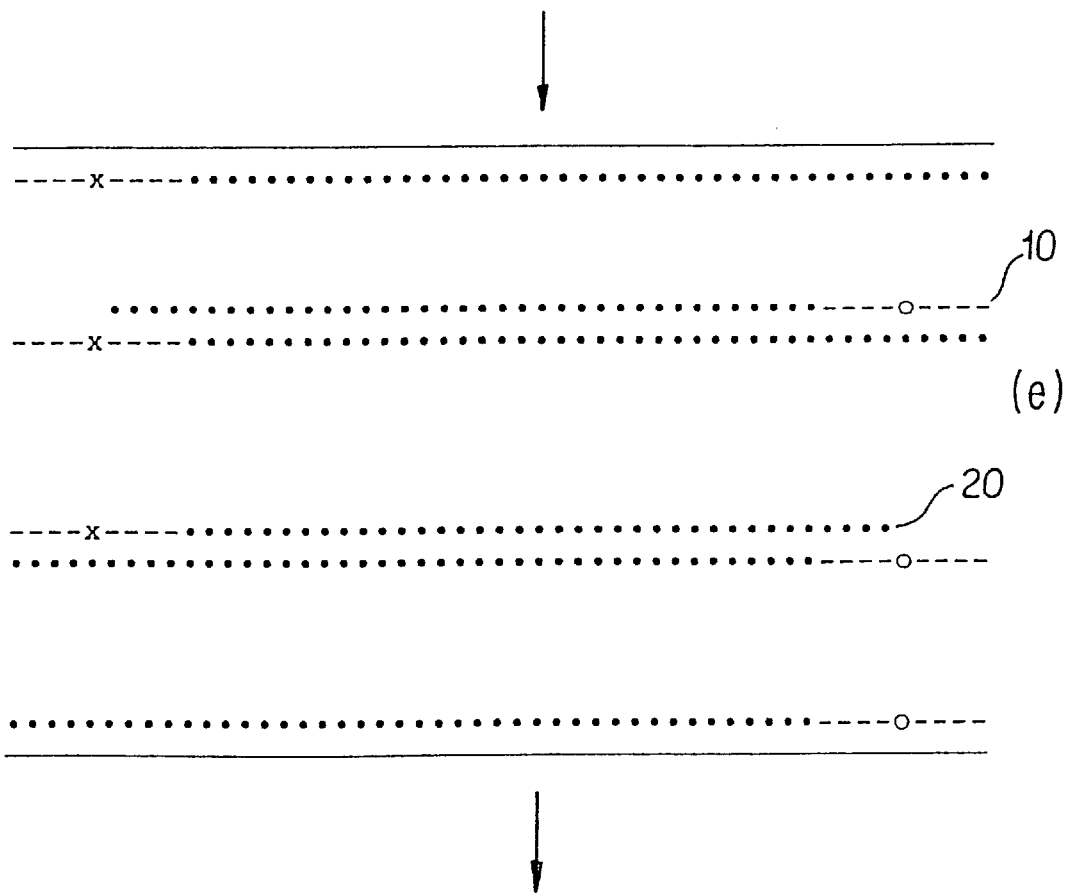
Figure 3:
Figure 4:
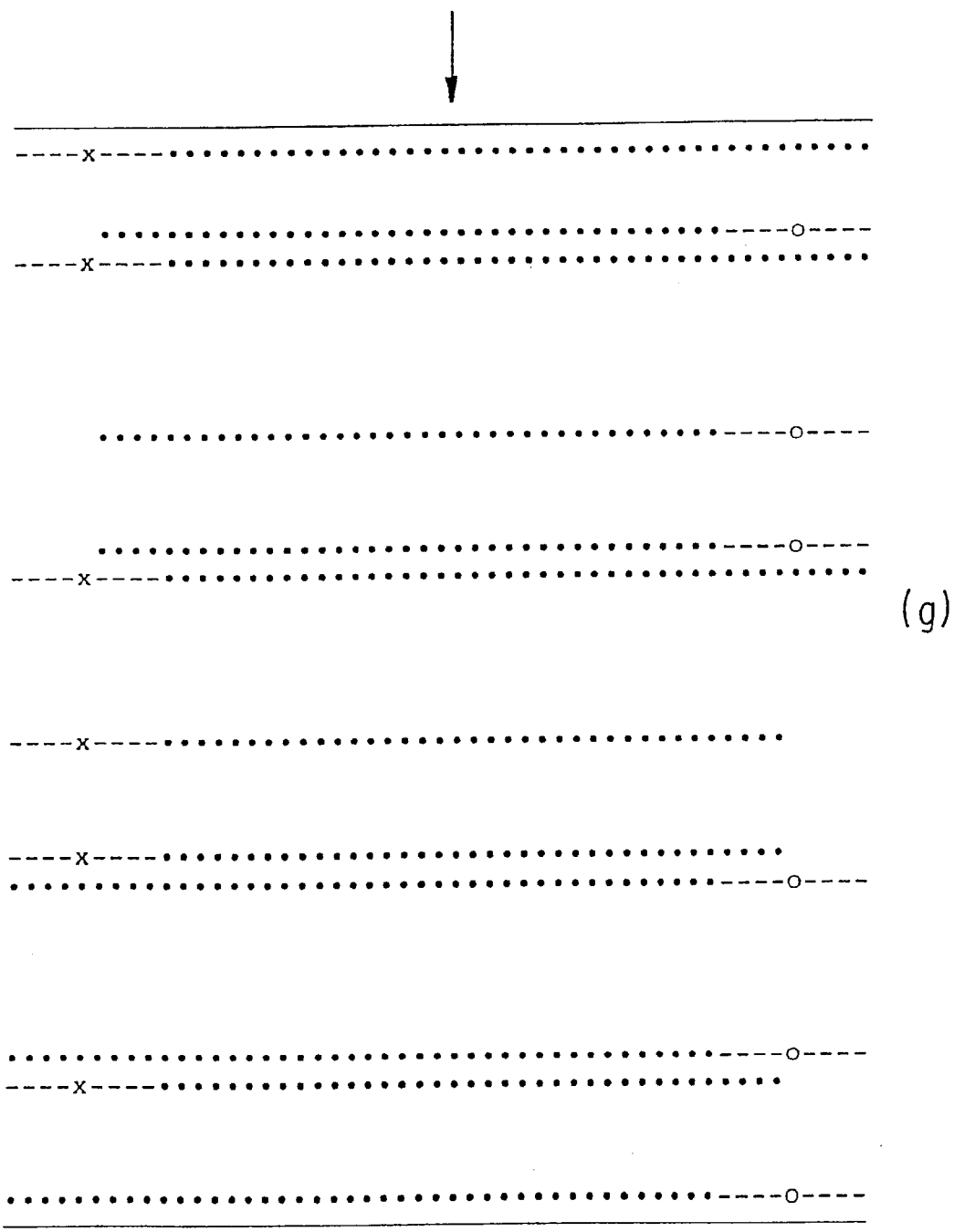

As seen in step (e) of FIG. 2, primer elongation using first generation DNA as a template results in the preparation of second generation DNA and does not progress past the non-replicable element incorporated into the first generation synthetic DNA. Thus, DNA molecules denoted by reference numerals 10 and 20 are synthesized. These second generation molecules do not participate further in the primer extension reaction because, as seen in the Figures, molecule 10 has not incorporated an effective binding site for the primer containing non-replicable or a cleavable element (x), and molecule 20 has not incorporated an effective binding site for the primer containing the non-replicable or cleavable element (o). Thus, as seen in steps (f) and (g), second generation molecules accumulate in a mathematically linear fashion in subsequent rounds of primer extension.

Figure 5:
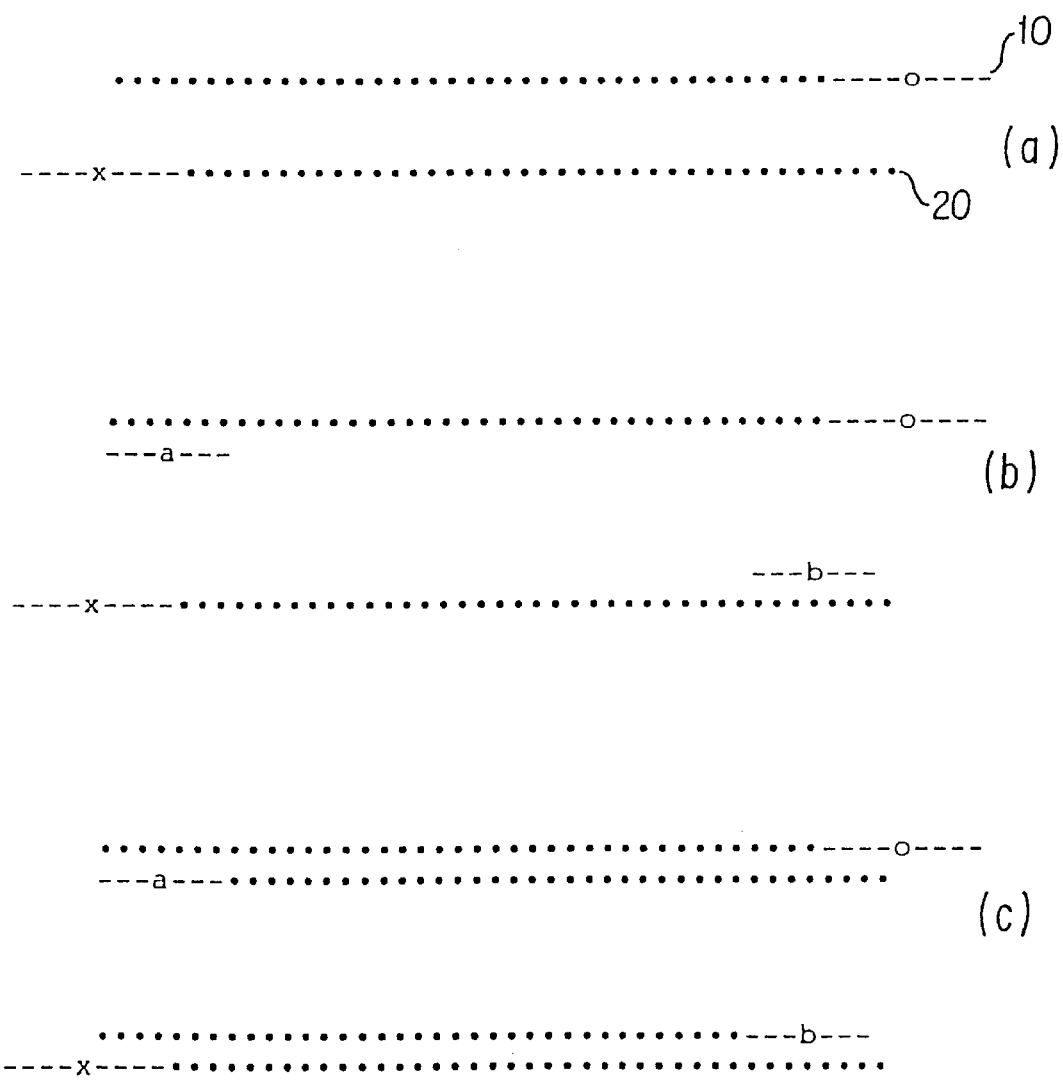
Figure 7A:
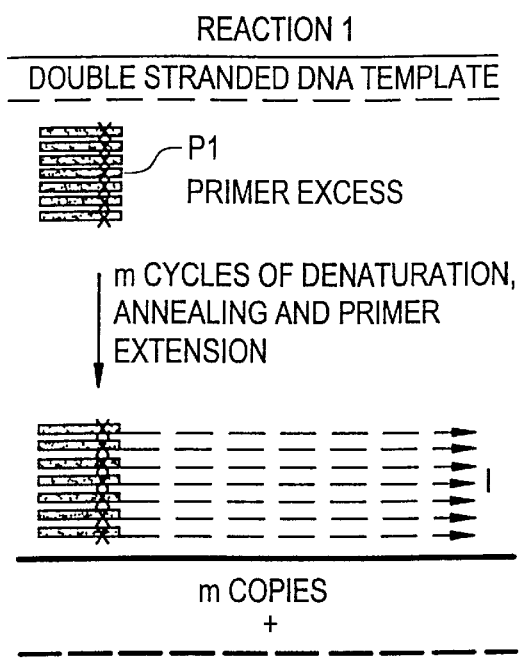
FIG. 7 is a more detailed schematic representation of a nucleic acid amplification process carried out with two primers according to the present invention.
Figure 7B:
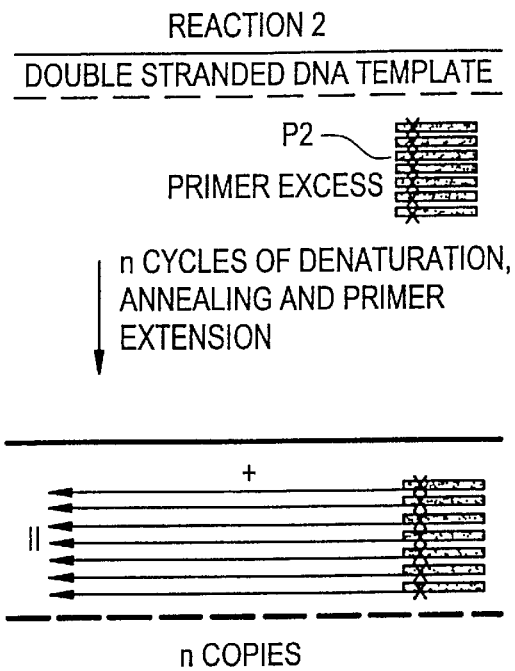
Figure 7C:
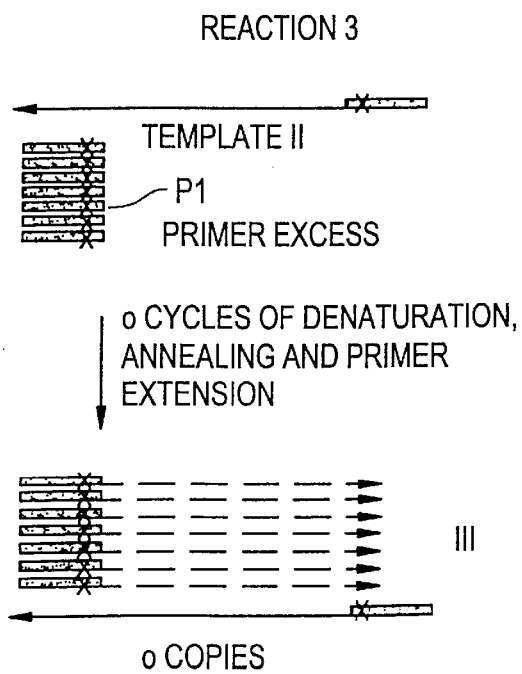
Figure 7D:
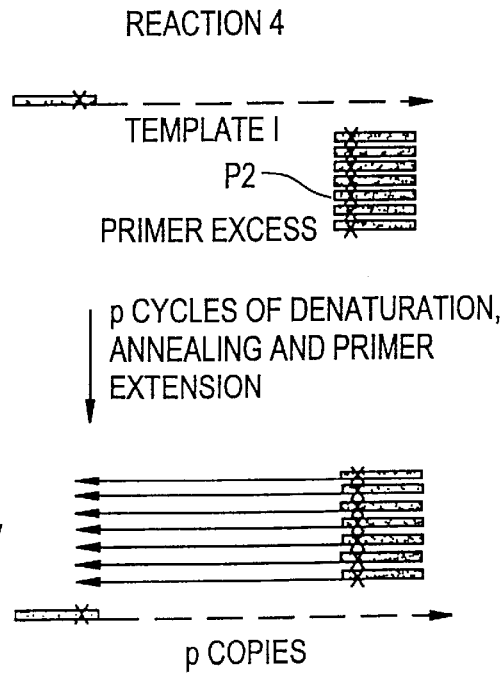
Figure 8A:
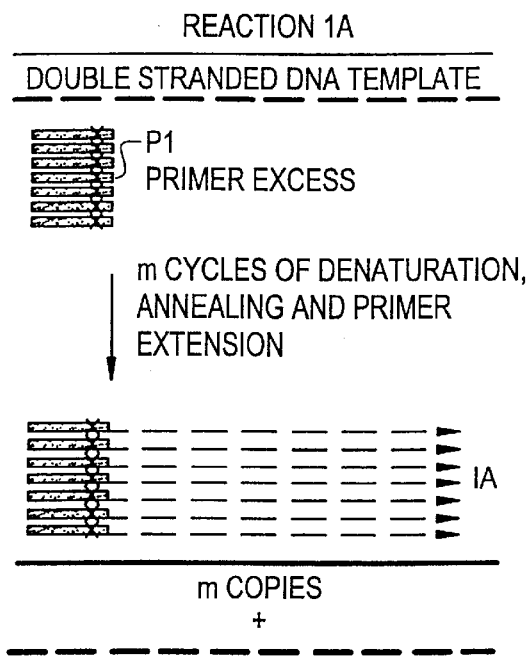
Figure 8B:
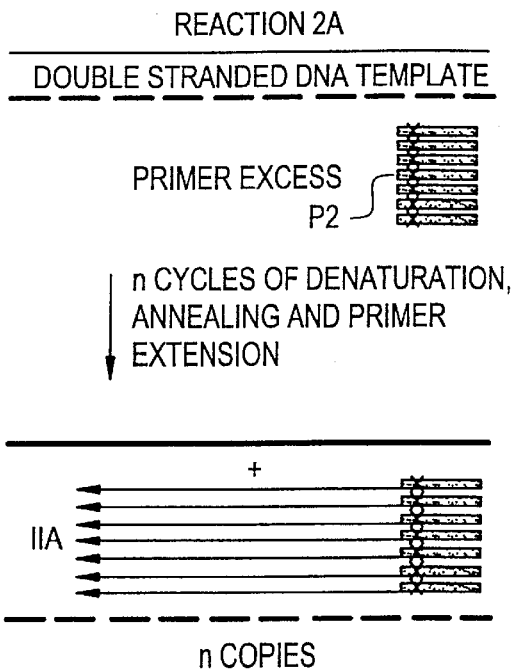
Figure 8C:
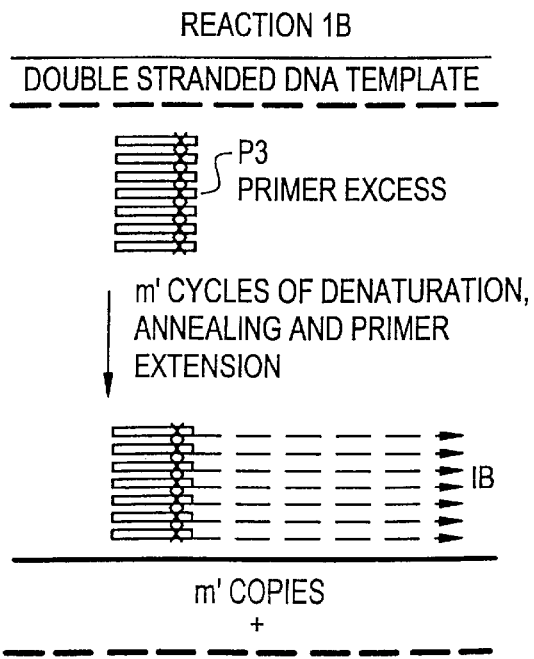
Figure 8D:
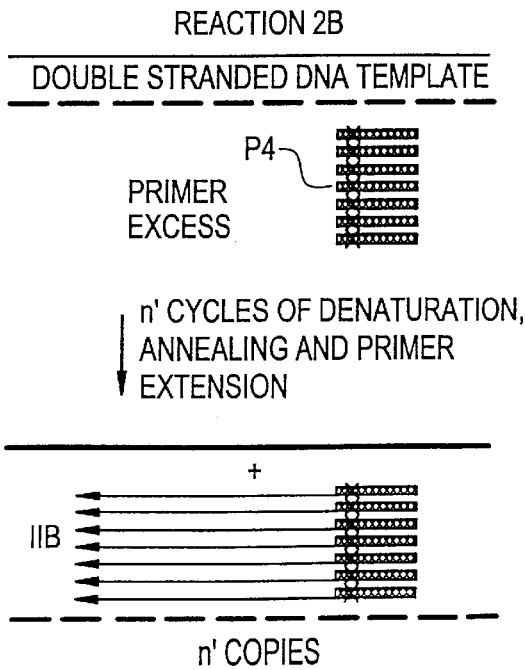

Following a desired number of cycles, the synthetic DNA is utilized as a starting material for (i.e., linked to) a second series of primer extension reactions using a second set of primers. As seen in FIGS. 5–6, primers containing non-replicable elements designated (a) and (b) are selected so as to be able to utilize molecules 10 and 20, the products of the reaction of FIGS. 1–4, as templates for further DNA synthesis. This series of primer extension reactions similarly results in the accumulation of synthetic DNA molecules, designated by reference numerals 30 and 40 in step (e) of FIG. 6, which cannot serve as templates for the primers utilized in those reactions. Following a desired number of cycles, these synthetic molecules can be linked to further replication using appropriate primers again containing non-replicable or cleavable elements. Where the primers contain cleavable elements, the first primer extension reaction is followed by a reaction in which the first primer extension product is cleaved at the position of the cleavable element, prior to the second primer extension reaction.

It should thus be apparent that the synthetic nucleic acid products of any one series of cycles can themselves serve as templates for further amplification only if a new primer or set of primers is provided. Thus, if a first linear amplification is performed for one hundred cycles, the one hundred copies produced from this reaction can be used as a template in a linked linear amplification (LLA) reaction using a new set of primers capable of hybridizing to the synthetic templates. One hundred additional cycles of linear amplification provides a cumulative amplification of ten thousand (100·100). Repeating the process with a third set of primers yields a cumulative amplification of $1 \times 10^6$. Additional amplification is achieved through the use of additional primers and additional cycles of primer extension.

FIG. 7 schematically illustrates, in greater detail, the use of two primers in an amplification process according to the present invention. With reference to the figure, two primers are utilized for sequential rounds of primer extension. Each primer is complementary to the target sequence but contains a single non-replicable element (X) in place of one of the complementary nucleotides.

There are four reactions to consider. In reaction 1, primer PI produces copies (first generation nucleic acid; product I) of the upper strand of the template. One copy of product I is produced during each cycle, m cycles leading to m copies. In reaction 2, primer P2 similarly produces copies (first generation nucleic acid; product II) of the lower strand of the template. One copy of product II is produced during each cycle, n cycles leading to n copies. In practice, n and m typically are the same.

In reaction 3, primer P1 produces copies (second generation nucleic acid; product II) of product II (designated template II) from reaction 2, except that template II is not replicated beyond the non-replicable element incorporated therein. Thus, product III is not a template for either primer P1 or P2.

Similarly, in reaction 4, primer P2 produces copies (second generation nucleic acid product IV) of template I, except that template I is not replicated beyond the non-replicable element. Thus, product IV is not template for either primer P1 or P2.

Table 1 shows the accumulation of each product as a function of cycle number. As can be seen, the equation $(n^2+n)/2$ can be used to calculate the yield of the reaction. If the efficiency of the reaction is less than 100%, amplification will be less.

for primer P1 or P2. As seen in reactions 5 and 6, however, primers P3 and P4, due to the location of their complementary site, can function to prime DNA synthesis on both original template DNA and templates IVA and IIIA, respectively. Meanwhile, products IIIB and IVB serve as templates for primers P4 and P3, respectively, and contain the nucleic acid sequence of interest.

It will be apparent that variations to the reactions described herein will be possible. For example, the linear amplification reactions can be sequentially linked, rather than being carried out simultaneously as described in connection with FIGS. 8–10. Thus, primers P3 and P4 can be added to the reaction mixture following n cycles of primer extension, where n ranges, for example, from 2 to 100.

TABLE 1

Accumulation of Products In a Two Primer LLA Reaction

| CYCLE (n) | I | Cumulative I | III | Cumulative III | Cumulative I + III | $(n^2 + n)/2$ |
|---|---|---|---|---|---|---|
| 1 | 1 | 1 | 0 | 0 | 1 | 1 |
| 2 | 1 | 2 | 1 | 1 | 3 | 3 |
| 3 | 1 | 3 | 2 | 3 | 6 | 6 |
| 4 | 1 | 4 | 3 | 6 | 10 | 10 |
| 5 | 1 | 5 | 4 | 10 | 15 | 15 |
| 6 | 1 | 6 | 5 | 15 | 21 | 21 |
| 7 | 1 | 7 | 6 | 21 | 28 | 28 |
| 8 | 1 | 8 | 7 | 28 | 36 | 36 |
| 9 | 1 | 9 | 8 | 36 | 45 | 45 |
| 10 | 1 | 10 | 9 | 45 | 55 | 55 |
| 11 | 1 | 11 | 10 | 55 | 66 | 66 |
| 12 | 1 | 12 | 11 | 66 | 78 | 78 |
| 13 | 1 | 13 | 12 | 78 | 91 | 91 |
| 14 | 1 | 14 | 13 | 91 | 105 | 105 |
| 15 | 1 | 15 | 14 | 105 | 120 | 120 |
| 100 | 1 | 100 | 99 | | | 5,050 |
| 200 | 1 | 200 | 199 | | | 20,100 |
| 500 | 1 | 500 | 499 | | | 125,250 |
| 1,000 | 1 | 1,000 | | | | 500,500 |

If a third primer containing a non-replicable element and complementary to either product III or product IV is included in the reaction, a new product, shorter than either product III or product IV will accumulate. This product will be in greater abundance than any other DNA strand in the reaction and will remain mostly single stranded.

Figure 10A:
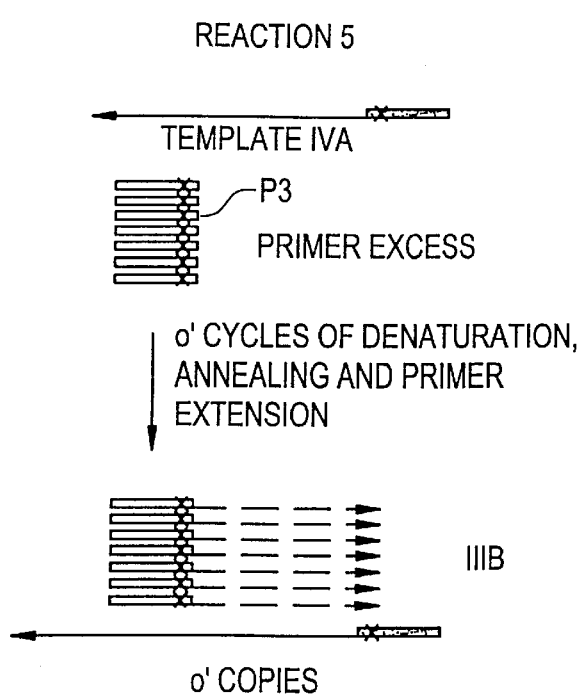
Figure 10B:
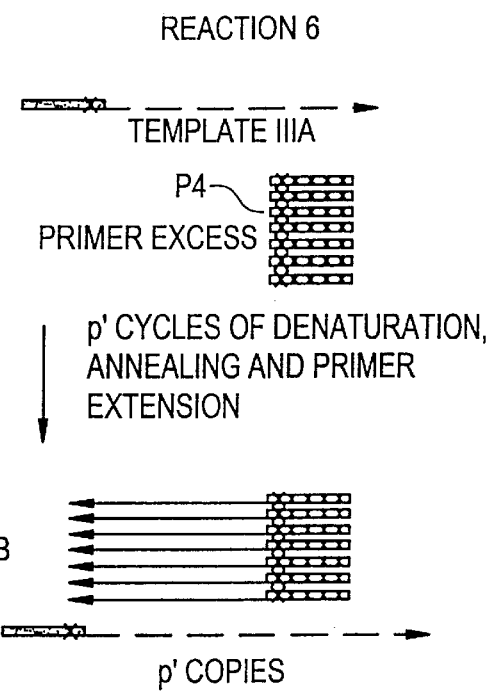

A reaction according to the present invention and "linking" linear amplification reactions together, to result in extensive DNA synthesis, is illustrated in FIGS. 8–10. Four primers are used in this reaction, thereby linking two two-primer reactions that are simultaneously carried out. In this reaction, primers P1 and P3 are complementary to the upper strand of the target nucleic acid and P2 and P4 are complementary to the lower strand. The complementary site for primer P3 is 5' (with respect to the template) of the P1 complementary site. Similarly, the complementary site for primer P4 is 5' (with respect to the template) of the P2 complementary site. The nucleic acid sequence of interest advantageously will be located within the region bounded by both primer pairs.

Six different reactions can be considered, each differing in the templates used, and are shown in the figures. Reactions 1A, 1B, 2A and 2B each result in the linear accumulation of first generation synthetic nucleic acid (products IA, IB, IIA and IIB, respectively) complementary to a respective strand of the starting nucleic acid template. Reactions 3A, 3B, 4A and 4B each result in the linear accumulation of second generation synthetic nucleic acid which, due to the presence of the non-replicable element in the nucleic acid synthesized in reactions 1A, 1B, 2A and 2B, does not serve as a template In another variation, primers P1 and P2 are selected so that they are capable of annealing to the template DNA and priming DNA synthesis under conditions (e.g., temperature) that do not permit primers P3 and P4 to prime. Primers P1, P2, P3 and P4 will be provided in the initial reaction mixture. The first linear amplification is carried out under the more stringent conditions, where only primers P1 and P2 participate in primer extension. Following a desired number of cycles, the reaction conditions are made less stringent, whereupon all four primers participate in nucleic acid synthesis. Primers P1 and P2 continue to generate first generation primer extension products using the starting template and second generation primer extension products using the first generation products as template; primers P3 and P4 also utilize second generation primer extension products of primers P1 and P2 as templates. Again, the nucleic acid sequence of interest advantageously is located within the region of the template strand bounded by both primer pairs.

If a fifth primer containing a non-replicable element and complementary to either product IIIB or product IVB is included in the reaction, a new product, shorter than either IIIB or IVB, will accumulate. This product will be in greater abundance than any other DNA strand in the reaction and will remain mostly single stranded. Those skilled in the field of molecular biology will realize that whenever an odd number of primers is utilized to practice this invention, an accumulation of single stranded DNA will result.

The use of primers that contain non-replicable and/or cleavable elements ensures that, except for primer extension products synthesized on an original template nucleic acid strand present in the starting material (such primer extension products being referred to herein as "first generation primer extension products"), none of the synthetic nucleic acids produced during the process will serve as templates in subsequent rounds of primer extension. Thus, the accumulation of synthetic nucleic acid in a mathematically exponential manner from cycle to cycle, as achieved in the context of the PCR reaction (Kleppe et al. and Saiki et al., supra), is avoided.

Scientists experienced in the field of molecular biology and DNA chemistry will be able to synthesize primers that contain non-replicable or cleavable elements. For example, primers that contain a residue of 1,3-propanediol (which halts the synthesis of DNA) can be synthesized according to the method described in Seela et al., *Nucleic Acids Res.* 15, 3113–3129 (1987) and are commercially available from Glen Research, 44901 Falcon Place, Sterling, Va., 20166, USA. Primers containing a residue of 1,4-anhydro-2-deoxy-D-ribitol, the model for the abasic site, can be synthesized with the assistance of Eritja et al., *Nucleosides & Nucleotides* 6, 803–814 (1987). Published European Patent Application 416,817 A2 (Imperial Chemical Industries PLC; Mar. 13, 1991) describes the synthesis of primers containing one or more 2' deoxyribofuranosyl naphthalene moieties as non-replicable elements between a primer sequence and a polynucleotide tail. The synthesis of oligonucleotide primers that contain other elements that halt polymerase-dependent copying of the template, such as derivatives of ribonucleosides and deoxyribonucleosides, will be apparent to those who are experienced in this field. The non-replicable element preferably is not located at the terminal residue of any of the primers.

Scientists experienced in the field of molecular biology and DNA chemistry will likewise be able to synthesize primers containing cleavable elements. For example, primers containing ribonucleosides can be routinely synthesized by those of skill in nucleic acid chemistry using standard methods of oligonucleotide synthesis by incorporating protected ribonucleotide in place of deoxyribonucleotides in oligonucleotide synthesis reactions known to those of skill in nucleic acid chemistry. Appropriate ribonucleoside containing primers are commercially available.

One method of cleaving first primer extension products utilizes the difference in reactivity of phosphodiester bonds adjacent to a ribonucleoside compared with the reactivity of phosphodiester bonds adjacent to deoxyribonucleosides. Primer extension products containing ribonucleotides can be easily cleaved by treating the products with, a ribonuclease (RNase), such as RNase A. If uridine triphosphate (UTP) is incorporated into the primer, the enzyme uracil N-glycosylase (UNG) can also be used to cleave the first primer extension product to remove its complementary primer hybridization site. Alternatively, primer extension products containing ribonucleosides can be cleaved by treating the products with hydroxide, preferably 0.5 N NaOH. Preferred primers will contain one or more ribonucleosides which will be located at a position in the primer so that cleavage will disrupt the hybridization site for one of the primers used in the subsequent primer extension reaction. The ribonucleoside can be located at the 3' terminus of the primer since, unlike the non-replicable element, it will not interfere with the DNA polymerase mediated extension reaction.

By way of example, a typical amplification reaction will be carried out starting with a double-stranded DNA molecule that contains a sequence to be replicated embedded within a much longer sequence. An oligonucleotide primer specific for each of the strands is annealed to its respective strand, with each primer containing a non-replicable and/or cleavable element as described herein. The primers are selected so that they bind to the respective strands at positions bounding the sequence to be amplified.

A first cycle of primer extension is carried out in the presence of a DNA polymerase and the four deoxyribonucleotide bases, under conditions appropriate for the selected enzyme. The resulting first generation synthetic DNA will have incorporated therein the oligonucleotide primer at its 5' end and the entire binding site for the other primer downstream (3') therefrom. Where the primer contains a cleavable element, the resulting first generation synthetic DNA will have incorporated therein the oligonucleotide primer containing the cleavable element or elements at its 3' end.

A second cycle of primer extension is carried out, wherein the first generation synthetic DNA serves as a template for the other primer, that is, the primer which is not incorporated at its 3' end. DNA synthesis progresses along the template, but halts when the non-replicable element embedded in the template is encountered by the polymerase molecule. The resulting synthetic DNA, herein termed "second generation synthetic DNA," has discrete ends defined at its 5' end by the entire sequence of its primer, and defined at its 3' end by only a portion of the sequence of the other primer—the portion that was copied by the DNA polymerase prior to encountering the non-replicable element.

Second generation synthetic DNA will not participate as a template for further DNA synthesis. As mentioned above, second generation synthetic DNA contains only a portion of the necessary primer binding site. Under the selected primer annealing and extension conditions, that portion of the primer binding site is insufficient to permit the primer to bind and serve as a site for primer-dependent DNA synthesis. Thus, when the third and subsequent cycles of primer extension are carried out, only original template DNA and first generation synthetic DNA participate as templates. The continued copying of those templates results in the round-to-round "linear" accumulation of second generation synthetic DNA containing the sequence of interest.

Following a desired number of primer extension cycles, additional replication can be attained by providing a second primer for each strand, the second primer(s) being selected so as to bind to regions of the original template strands within the region bounded by the original set of primers. The second primers, too, will contain non-replicable and/or cleavable elements, thereby ensuring that their primer extension products cannot serve as templates for nucleic acid synthesis in subsequent rounds using those same primers. Where the second primers contain cleavable elements, the first primer extension products made using these primers will cleaved at the position of the cleavable elements, such that second primer extension products produced from the first will not contain a functional binding site from which new copies identical to the first strand primer can be generated.

It is known that primer binding conditions, especially temperature, can dictate whether a specific primer will bind to a specific template. See Rychlik et al., *Nucleic Acids Res.* 18, 6409–6412 (1990); Wu et al., *DNA Cell Biol.* 10, 233–238 (1991). Thus, in a reaction mixture containing primers of various base composition and/or lengths, the selection of a primer binding temperature can also function to select which primers will be capable of priming DNA synthesis. For example, by providing first, second and third sets of primers that will prime at 72°, 62° and 52° C., respectively, in a single amplification reaction mixture, carrying out a first series of primer extension reactions at 72° C. will ensure that only the first primer set will function to bring about primer-dependent nucleic acid synthesis. Following a desired number of cycles, the primer extension temperature can be lowered to 62° C., whereupon the first and second primer sets will prime DNA synthesis. Lowering the primer extension reaction temperature to 52° C. permits all three primer sets to participate in primer-dependent DNA synthesis. The use of mixtures of primers in the present process permits the process to be carried out in an efficient manner, without the need for the researcher separately to add each primer set as the process progresses.

Through the use of available, programmable thermal cycling apparatus, all three primer sets as described above can be provided in a single amplification reaction mixture. The primers will be selected so that those that prime DNA synthesis under the most stringent conditions bind to the template 3' of the other primers. Similarly, those primers which prime under the least stringent conditions bind to the template 5' of the other primers.

A first series of primer extension reactions (cycles) are carried out under the most stringent (highest temperature) primer annealing conditions, whereupon only the first set of primers participate in the synthesis of DNA containing the sequence of interest. Following a pre-selected number of primer extension cycles, the primer annealing conditions are made less stringent. The second set of primers will initiate further DNA amplification by priming the linear copying of the second generation synthetic DNA produced during the first series of primer extension cycles under the selected conditions. When the conditions are further adjusted so that the third set of primers can participate in primer-dependent DNA synthesis, the second generation synthetic DNA's produced in both the first and second series of primer extension reactions serve as templates for DNA replication.

The design of primers that bind at preselected temperatures is within the skill of molecular biologists. The temperature at which a specific primer will function can be predicted by available algorithms (Wu et al., DNA Cell Biol. 10, 233–238 (1991)) and by computer programs (Rychlik et al., Nucleic Acids Res. 18, 6409–6412 (1990)), based upon primer length and base composition.

Appropriate temperature cycling for in vitro DNA amplification can be performed manually or by commercially-available, programmable thermal cycler apparatus. Very fast cycle times can be achieved using hot air cyclers (Wittwer et al., Nucleic Acids Res. 17, 4353–4357 (1989)); cycle times as short as thirty seconds are possible (Wittwer et al., Biotechniques 10,76–83 (1991)). Thus, one hundred cycles of primer extension can be achieved in as little as about fifty minutes.

Appropriate temperature cycling which inactivates the reagent used to cleave first primer extension products can be incorporated into programs used with programmable thermal cycling apparatus for carrying out desired amplification reactions. For example, the activity of most RNases is destroyed by heating reaction mixtures containing RNase to 100° C. for 3 to 5 minutes.

Alternatively, all of the primers in a series of nested primers can be simultaneously provided in a single amplification reaction mixture with the reaction being carried out under primer annealing conditions whereby each set of primers is capable of binding to the respective complementary site. Performance of n cycles of the primer extension reaction results in accumulation of products which contain the nucleic acid sequence of interest, although the products will differ in length depending upon the position of the initial primer with respect to the sequence of interest on the nucleic acid strands to be amplified.

Allele-Specific Linear Amplification

In one embodiment of the present invention, a primer is designed such that its 3' nucleotide is complementary to a particular nucleotide in the template known to be variable (polymorphic). The variable nucleotide can be a nucleotide involved in a genetic disease such as sickle cell anemia, or at another site known to be polymorphic.

If a mismatch is present between the 3' nucleotide of the primer and the corresponding nucleotide of the template DNA, the primer design insures that it will be extended poorly, or, preferably, not at all. See Petruska et al., PNAS USA 85, 6252–6256 (1988). Thus, such a primer is "allele specific" and capable of discerning the presence of absence of a single base within a nucleic acid sequence of interest. The presence of synthetic DNA following the use of an allele-specific primer in the process according to the present invention thus is indicative of the presence of the allele of interest in the original DNA template.

This allele-specific characteristic of oligonucleotide priming has been used to perform allele- specific PCR. See, for example, Newton et al., Nucleic Acids Res. 17, 2503–2516 (1989). As is the case with PCR in general, however, the exponential behavior of the allele-specific PCR reaction has been associated with difficulties in running the reaction (see Ugozzoli et al., Methods 2, 42–48 (1991)). The cycle-to-cycle linear behavior of the present amplification process, due to the presence of a non-replicable element within the allele-specific primer(s), avoids such difficulties, however.

Detection of Amplified Products

The primary products of the amplification process of the present invention are single-stranded synthetic DNA's of a defined length. The length of the product strand is determined by the position of the last-used primer and is equal to the sum of the length of the primer itself and the number of nucleotides which can be incorporated from the 3' end of the primer to the non-replicable element of the template. The products can be detected by known nucleic acid detection techniques, including the use of primers or probes labeled with radioactivity, a fluorescent moiety or an enzyme, etc., electrophoresis, high pressure liquid chromatography, etc.

The present invention will have important application in the diagnosis of human and other animal genetic diseases. Many human genetic diseases are known to be caused by specific changes in genes of known sequence. For these specific mutations, DNA-based diagnosis is possible using hybridization or other allele specific technologies (see above) to determine which of the various gene sequences are present in the DNA of a person at risk for the disease(s). Clearly, amplification of target DNA has been very helpful in developing these technologies. The main advantages of template amplification are: smaller sample sizes can be used, the signal to noise ratio of the detection system is improved, there is a real potential for automation and the amplification system itself can be the detection system.

The processes of the present invention offer all of the same advantages offered by other amplification reactions, plus additional benefits. The products are single stranded and thus do not have to be denatured prior to detection. If an odd number of primers is used, excess single stranded molecules will be produced. These molecules will be useful, for example, as hybridization probes, and thus provide an additional advantage over other amplification technologies. Still further advantages are presented as the products accumulate linearly and thus can be accurately quantified; the occurrence of "false positives" will be reduced in comparison with exponential processes that use newly-synthesized DNA as a template in subsequent rounds using the same primer.

Those skilled in the art will recognize that the DNA template to be amplified according to the invention can be from a variety of sources. The template DNA, for example, can be derived from mRNA by use of reverse transcriptase. While most polymerases prefer to copy DNA templates, reverse transcriptase (RNA-dependent DNA polymerase) can be utilized to synthesize double stranded DNA copies of RNA templates using procedures well known to those skilled in the art.

EXAMPLES

Solutions utilized in several of the following examples are described below:

TE (Tris-EDTA): 10 mM Tris-HCl, 1 mM EDTA. pH 8.0

TBE (Tris-Borate-EDTA): 89 mM Tris-HCl, 89 mM Boric Acid, 2 mM EDTA, pH 8.3

Klenow polymerase Buffer: 50 mM Tris-HCl, 10 mM $MgCl_2$, pH 7.6

Kinase Buffer: 50 mM Tris-HCl, 10 mM $MgCl_2$, 5 mM DTT, 0.1 mM spermidine-HCl, 0.1 mM EDTA, pH 7.6

DNA Polymerase I buffer: 50 mM Tris-HCl, 10 mM $MgSO_4$, 0.1 mM DTT, 50 μg/ml bovine serum albumin, pH 7.2

Sequenase buffer: 40 mM Tris-HCl, 20 mM $MgCl_2$, 50 mM NaCl, pH 7.5

Bst polymerase buffer: 20 mM Tris-HCl, 20 mM $MgCl_2$, pH 8.5

*Thermus aquaticus* polymerase buffer: 50 mM KCl, 10 mM Tris-HCl, 1.5 mM $MgCl_2$, 0.01% w/v gelatin, pH 8.3

10×Ficoll loading buffer: 100 mM Tris-HCl pH 7.5, 10 mM EDTA, 0.5% bromophenol blue, 0.5%; xylene cyanol, 30% Ficoll 5×SSPE: 50 mM sodium phosphate pH 7.0, 0.9 mM NaCl and 5 mM EDTA 6×SSC: 0.9 M NaCl, 0.09 M sodium citrate The inventive process is illustrated by the following examples, which do not limit the scope of protection sought.

Example 1
1,3 Propane Diol Blocks Primer Extension When Present in a Template A template with or without a single nucleotide base containing a 1,3 propane diol moiety (designated as non-replicable element "X") and a primer complementary to the 3' end of the template were synthesized in order to demonstrate the ability of the 1,3 propane diol moiety to serve as a non-replicable element and halt DNA synthesis. The sequences synthesized are as follows:

| | | | |
|---|---|---|---|
| DNA II 207 | GCTCCTTAGCATGGGAGAGTCTCCGGTTC | | SEQ ID NO:2 |
| DNA II 207X | GCTCCCTTAXCATGGGAGAGTCTCCGGTTC | | SEQ ID NO:3 |
| P12 | GAACCGGAGACT | | SEQ ID NO:4 |

The primers and templates were annealed to form the following primer template complexes:

```
5' GCTCCCTTAGCATGGGAGAGTCTCCGGTTC
              TCAGAGGCCAAG 5'

5' GCTCCCTTAXCATGGGAGAGTCTCCGGTTC
              TCAGAGGCCA-AG 5'
```

The primer template complexes were then extended with various DNA polymerases (Klenow fragment of DNA Polymerase I, AmpliTaq polymerase (Perkin Elmer—Cetus Corp.), BST polymerase (Bio-Rad Laboratories, Hercules, Calif.) and Sequenase polymerase (United States Biochemical, Cleveland, Ohio) in the presence of α-[$^{32}$P]-dCTP and the products were subjected to electrophoresis on a denaturing polyacrylamide gel.

The primer and templates were mixed at a primer/template ratio of 10, and buffers appropriate for the polymerase enzymes were employed. Twenty μl reactions containing 1 pmol of either 207 or 207-X, 10 pmol P12, 25 μM dNTPs, 0.5 μCi of α-[$^{32}$P]-dCTP and either AmpliTaq buffer, BST buffer, Klenow buffer or Sequenase buffer. The samples were heated at 90° C. for two minutes and cooled to 0° C. for five minutes before adding one unit of DNA polymerase and reacting at 37° C. for 10 minutes. The results indicate that the propane diol residue blocks primer elongation for-all four DNA polymerases as shown below:

```
5' GCTCCCTTAGCATGGGAGAGTCTCCGGTTC
>              TCAGAGGCCAAG 5'
5' GCTCCCTTAXCATGGGAGAGTCTCCGGTTC
>              TCAGAGGCCAAG 5'
```

Example 2
Primers with Propane Diol-Containing Base Do Not Support PCR

Four oligonucleotides were prepared, two of which contained the non-replicable 1,3-propane diol moiety. The sequences were synthesized on an Eppendorf Ecosyn D300, automated DNA synthesizer with the MMT-propane diol phosphoramidite in the Z position. When entering the sequence into the synthesizer, a Z was introduced. The sequences are presented in the following table:

| | | | |
|---|---|---|---|
| BGP-2 22 | GGGTGGGAAAATAGACCATAG | | SEQ ID NO:5 |
| BGP-2 22X | GGGTGGGAAAATAGACCXATAG | | SEQ ID NO:6 |
| BGP-1 30 | GGCAGGAGCCAGGGCTGGGCATAAAAGTCA | | SEQ ID NO:7 |
| BGP-1 30X | GGCAGGAGCCAGGGCTGGGCATAAAXGTCA | | SEQ ID NO:8 |

The sites of complementarity of the oligonucleotides in the human β-globin gene (GenBank Locus HUMHBB) is shown in FIG. 12 (SEQ ID NO: 1).

In vitro amplification reactions were performed with various combinations of the four primers. Each reaction contained 100 ng of human genomic DNA, 6 pmol of each of two primers, in a standard PCR reaction buffer. Reactions were placed in a thermal cycler (Ericomp) and heated to 94° C. for three minutes, cooled to 55° C. for 30 seconds, heated to 72° C. for 30 seconds and then subjected to 31 cycles of heating and cooling as follows: 94° C., one minute, 55° C., 30 seconds, 72° C. for 30 seconds. Following thermal cycling the sample was incubated at 72° C. for an additional 3.5 minutes. Only the reaction containing the primers without propane diol (BGP-1 30 and BGP-2 22) gave a 319 bp amplification product. Thus it was confirmed that the propane diol-containing primers do not support PCR.

Example 3
Propane Diol-Containing Primers Produce Specific DNA Fragments

The plasmid pHβ$^A$ was mixed with propane diol- containing primers (BGP-1 30X and BGP-2 22X) or control primers (BGP-1 30 and BGP-2 22) not containing propane diol moieties. The primer/template mixtures were subjected to thermal cycling conditions of 94° C. for 20 seconds to dissociate the double-stranded template, followed by 48° C. for 20 seconds. After the final cycle, the reaction mixtures were incubated a further 5 minutes 40 seconds at 48° C. to complete the primer extension reaction and anneal the single stranded DNA's. The reaction mixtures employing the propane diol-containing primers (according to the present invention) were cycled through 45 rounds of primer extension. The PCR reactions, utilizing the primers not containing propane diol moieties were cycled through 10 rounds of primer extension. The products of the reactions were subjected to electrophoresis on 1.5%; agarose (TBE buffer). The propane diol-containing primers produce a DNA fragment which was smaller than the PCR generated fragment. The smaller size is due to the fact that the primer extension does not extend to the end of the template strand, leaving 5' extensions on the product.

FIG. 11 presents a comparison of the products of a PCR reaction and of an LLA reaction according to the present invention. The major products of a PCR reaction, which accumulate exponentially, are completely double-stranded with defined ends corresponding to the ends of the primers employed. The products of the present process, however, are shorter than corresponding PCR products, as primer extension past the non-replicable element does not occur.

Example 4
Propane Diol-Containing Primers Support DNA Amplification

An amplification reaction according to the present invention was performed using BGP-1 30X and BGP-2 22X for various numbers of cycles. The products of the amplification were subjected to dot blot hybridization, and the hybridization signal was compared to that obtained from a known amount of plasmid DNA containing the sequence.

Fifteen μl reactions were prepared containing 1.1 ng of the plasmid pHβ$^A$ (containing the entire human β-globin gene cloned in pBR322), 5 pmol of BGP-1 30X, 5 pmol of BGP-2 22X, 83 μM dNTPs, 2.5 units AmpliTaq® DNA polymerase in a standard PCR buffer. Thermal cycling reactions were performed in a Corbett Research FTS-1 thermal cycler for 45, 32 and 22 cycles with the following program: 94° C. 20 seconds, 48° C. 20 seconds. At the end of the cycling the reactions were heated to 94° C. for 20 seconds and then incubated at 48° C. for four minutes.

The products of the reactions (3 μl) were mixed with 10 μl 4N NaOH, 250 mM EDTA and were blotted onto a Zeta-Probe membrane (Bio-Rad Laboratories, Hercules, Calif.). Also included on the membrane was 56, 118 and 231 ng of the plasmid pHβ$^A$ similarly denatured. The membrane was hybridized with 5'-$^{32}$P-CTGCAGTAACGGCAGACTTCTCCT (SEQ ID NO: 9) at 55° C. for three hours in 5×SSPE, 1%. SDS, 5 mg/ml Blotto, 10 μg/ml Homomix I RNA. After hybridization the blot was washed at room temperature in 6×SSC and then scanned in a Bio-Rad Molecular Imager. The reaction produced approximately 250 fold amplification demonstrating the process of the present invention results in the amplification of the nucleic acid sequence of interest.

Example 5
Amplification of the Human β-Globin Gene from Genomic DNA

Linear amplification reactions were performed according to the present invention in a 15 μl volume containing Thermus aquaticus polymerase buffer, template DNA (800 ng of genomic DNA or 10$^4$ molecules of plasmid pHβ$^A$), 200 μM each dNTP (dATP, dTTP, dCTP, and dGTP), 2 pmol of oligonucleotide primers BGP5-22X and BGP4-22X, and 2 units of Ampli-Taq Polymerase (Perkin-Elmer Cetus). Plasmid pHβ$^A$ contains a 4.4 kb Pst I fragment of the human β-globin gene cloned at the Pst I site of pBR322. As a negative control, a reaction was carried out which included all the ingredients used in the previous reactions except the template DNA (a "no template" control). After denaturing the template DNA for 3 min, the amplification was performed for 99 cycles as follows: annealing at 55° C. for 30 sec, polymerization at 72° C. for 15 sec, and denaturation at 94° C. for 30 sec. At the end of the last cycle, the samples were annealed at 55° C. for 30 sec and finally polymerized at 72° C. for 4 min.

At the end of the first step (100 cycles), 7.5 μl were removed from each sample (genomic DNA, plasmid DNA, and negative control), and 'mixed with 7.5 μl containing Thermus aquaticus polymerase buffer, 5 pmol of primers BGP1-35X and BGP2-35X, and 2 units of Ampli-Taq Polymerase. The cycling program was similar to the program used in the first step, except that the annealing temperature was 63° C.

To control the size of the fragments generated by the amplifications, two reactions were performed. One reaction contained Thermus aquaticus polymerase buffer, 5 pmol of primers BGP5-22X and BGP4-22X, 1×10$^8$ molecules of plasmid pHβ$^A$, and 3 units of Ampli-Taq Polymerase. The second control included the same ingredients as the previous reaction except that the primers BGP1-35X and BGP2-35X were used. The template DNA was denatured for 4 min at 94° C. and then cycled 48 times using the following conditions program: annealing and polymerization at 55° C. for 30 sec; denaturation at 94° C. for 30 sec. At the end of the last cycle the samples were annealed at 55° C. for 30 sec and polymerized at 72° C. for 4 min.

```
BGP1-35X CCAGGGCTGGGCATAAAAGTCAGGGCAGAGXCATC  SEQ ID NO:10

BGP2-35X GGGTGGGAAAATAGACCAATAGGCAGAGAGXGTCA  SEQ ID NO:11
```

Analysis of the LLA Products

The entire reaction (15 μl) was mixed with 1.6 μl 10×Ficoll loading buffer and subjected to electrophoresis in a 1.5% agarose gel (Bio-Rad ultrapure agarose). Electrophoresis was performed in TBE buffer for 90 min at 110 volts. The gel was subsequently stained with ethidium bromide (1 μg/ml) for 30 min, destained for 15 min, and photographed by ultraviolet (UV) illumination. The electrophoresed DNA was then transferred to a nylon membrane (Zeta probe, Bio-Rad) by alkaline transfer (Reed, K. C. and D. A. Mann, Rapid transfer of DNA from agarose gels to nylon membranes, Nucleic Acids Res. 13:7207–7221 (1985)) and fixed to the membrane by UV radiation (Church, G. M. and W. Gilbert, Genomic Sequencing, Proc. Natl. Acad. Sci. U.S.A. 81:1991–1995 (1984)). The membrane was prehybridized in 5×SSPE, 1% SDS, 10 μg/ml homomix RNA and 0.5% dehydrated powdered skim milk (Carnation, Los Angeles, Calif.) for one hour and subsequently hybridized with 2.5×10⁶ cpm/ml 5' end $^{32}$P labeled probe 5'CAG-GAGTCAGGTGCACCATGGT (SEQ ID NO: 14) for two hours at 55° C. The membrane was washed twice with 6×SSC for 30 min at room temperature and autoradiographed at room temperature for 30 min.

The genomic DNA produced the same fragment as the globin gene plasmid DNA control. The size of the fragment is that produced by the BGP1-35X and BGP2-35X primers.

Example 6

LLA Amplification Products are Resistant to Contamination in Comparison with PCR In Vitro Amplifications The "LLA" amplification reaction of the present invention was carried out in a 15 μl volume containing *Thermus aquaticus* polymerase buffer, template DNA (3.5×10⁹ molecules of plasmid pHβ$^A$), 200 μM each dNTP (dATP, TTP, dCTP, and dGTP), 5 picomoles of oligonucleotide primers BGP1-22X and BGP2-22X, and 1.25 units of Ampli-Taq DNA Polymerase (Perkin-Elmer Cetus). After denaturating the template DNA for 1 min, the amplification was performed for 49 cycles by annealing at 48° C. for 30 seconds and denaturing at 94° C. for 30 seconds. At the end of the last cycle, the samples were incubated at 48° C. for 4 min.

The PCR reaction was performed for comparison purposes in a 15 μl volume containing *Thermus aquaticus* polymerase buffer, template DNA (3.5×10⁹ molecules of plasmid pHβ$^A$) 200 μM each dNTP (dATP, TTP, dCTP, and dGTP), 5 picomoles of oligonucleotide primers BGP1-22 and BGP2-22, and 1.25 units of Ampli-Taq DNA Polymerase. After denaturating the template DNA for 1 min, the amplification was performed for 9 cycles by annealing at 48° C. for 30 seconds and denaturing at 94° C. for 30 seconds. At the end of the last cycle, the samples were incubated at 48° C. for 4 min.

Analysis of the LLA and PCR Products

Two fold serial dilutions of the LLA and PCR products (1/64 μl, 1/32 μl, 1/16 μl, 1/8 μl, 1/4 μl, 1/2 μl, 1 μl, 2 μl, 4 μl, and 8 μl) were mixed with 1×Ficoll loading buffer and subjected to electrophoresis in a 1.5% agarose gel. Electrophoresis was performed in 1×TBE buffer for 90 min at 110 volts. The electrophoresed DNA was transferred to a nylon membrane by alkaline transfer (Reed and Mann, 1985), cross linked by UV radiation (Church and Gilbert, 1984), and then neutralized with 2×SSC. Subsequently, the membrane was hybridized in 5×SSPE, 1% sodium dodecyl sulfate (SDS), 10 μg/ml homomix RNA, 0.5% powdered skim milk and 2.5× 10⁶ cpm of the $^{32}$P labeled probe 5' CAGGAGTCAGGTG-CACCATGGT. The hybridization took place at 55° C. for two hours. After hybridization, the membrane was washed twice with 6×SSC at room temperature for 15 min. and then scanned and quantified with the Bio-Rad GS-250 Molecular Imager.

Amplicon Contamination Experiments

Equal amounts of LLA (1/26 μl) and PCR (1/16 μl) products (as quantified with the imager (above)) were diluted with distilled water by 10⁴, 10⁵ and 10⁶ fold; these dilutions were subsequently used as DNA templates in PCR reactions. The amplification reactions were performed in a 15 μl volume containing *Thermus aquaticus* polymerase buffer, template DNA (LLA or PCR dilutions), 200 μM each dNTP (dATP, TTP, dCTP and dGTP), 5 picomoles of oligonucleotide primers BGP1-22 and BGP2-22, and 1 unit of Ampli-Taq Polymerase. Reactions were duplicated and after a first step of thermal denaturation for 3 min at 94° C., the samples were run for 25 and 30 cycles of amplification (30 seconds at 55° C., 30 seconds at 72° C., and 30 seconds at 94° C.) and finally incubated at 50° C. for 30 seconds and 4 min at 72° C. Furthermore, a negative control which contained all reagents except the template DNA was included.

To control and quantify the relative amounts of LLA and PCR DNA templates, a second PCR reaction set was performed using a different primer set (MD040 and PC04) which prime internally to BGP1-22 and BGP2-22. The reaction ingredients (except the primers) and reaction conditions were as described in the previous paragraph.

The 15 μl reaction volumes were mixed with 1.6 μl 10×Ficoll loading buffer and subjected to electrophoresis in a 1.5% agarose gel (Bio-Rad ultrapure agarose). Electrophoresis was performed in 1×TBE buffer for 90 min at 110 volts. The gel was subsequently stained with ethidium bromide (I μg/ml) for 30 min, destained for 15 min, and photographed by ultraviolet (UV) illumination. The electrophoresed DNA was then transferred to a nylon membrane by alkaline transfer (Reed and Mann (1985)) and fixed to the membrane by UV radiation (Church (1984)). The membrane was prehybridized in 5×SSPE, 1% SDS, 10 μg/ml Homomix RNA and 0.5% dehydrated powdered skim milk for one hour and subsequently hybridized with 2.5×10⁶ cpm/ml of the 5'-P$^{32}$ labeled probe 5' CAGGAGTCAGGTGCAC-CATGGT for two hours at 55° C. The membrane was washed twice with 6×SSC for 30 min at room temperature and the reactions were quantified with the Bio-Rad GS-250 Molecular Imager.

Results

The ratio of hybridization of reactions amplified with the outside primer set (measuring the ability of the amplicon to amplify in the second reaction) to the inside primer set (measuring the amount of amplicon present in the reaction) was determined. As can be seen from the following table, LLA reactions produce an amplicon which is very resistant to amplification from the outside primers and therefore will be resistant to the effects of carry over contamination.

TABLE II

Effect of Contamination On Subsequent Amplification

| Dilution | Outside:Inside (PCR) | Outside:Inside (LLA) |
|---|---|---|
| 10⁻⁴ | 1.58 | 0.17 |
| 10⁻⁵ | 1.62 | 0.02 |

Example 7

The Use of Ribonucleoside-Containing Primers to Produce Specific DNA Fragments by LLA Oligonucleotides and ribonucleoside containing oligonucleotides of the following sequences were prepared using standard automated solid-phase synthesis methods. The uracil nucleoside in oligonucleotides GH1 and GH2 are ribonucleosides.

| GH1 SEQ | TTCCCAACCAUTCCCTTA | SEQ ID NO:16 |
| GH2 SEQ | GGATTTCTGUTGTGTTTC | SEQ ID NO:17 |
| GH3 SEQ | TTCCCAACCATTCCCTTA | SEQ ID NO:18 |
| GH4 SEQ | GGATTTCTGTTGTGTTTC | SEQ ID NO:19 |
| Md114 | TAGCGTTGTCAAAAAGCC | SEQ ID NO:20 |

In vitro amplification reactions were performed to amplify a fragment of the human growth hormone gene from genomic DNA samples using either ribonucleoside containing primers GH1 and GH2 or deoxy-primers GH3 and GH4. Each reaction contained 500 ng of human genomic DNA, and 40 picomoles of each of two primers in a standard PCR reaction buffer which contained 1.5 units of Taq polymerase (Perkin-Elmer). The amplification reaction was carried out by placing the reaction mixtures into a thermal cycler, and heating to 95° C. for 4 minutes, cooling to 52° C. for 2 minutes, then heating to 72° C. for 1 minute. The amplification reaction was continued for 28 cycles as follows: 94° C. for 4 minutes, 52° C. for 2 minutes and 72° C. for 1 minute; and then for one cycle as follows: 94° C. for 1 minute, 52° C. for 2 minutes and 72° C. for 6 minutes. Following the reaction, amplified products were resolved on a 1.5% agarose gel, and then purified using "Prep-A-Gene" DNA purification kit (available from Bio-Rad.)

The amplified products, in a reaction volume of 5.6 µl, were treated with 1.4 µl of 0.5 M NaOH to cleave the amplification products at the phosphodiester bond adjacent to the uracil ribonucleoside which had been incorporated into the first PCR product, then heated to 95° C. for 15 minutes. These solutions were neutralized by adding 0.9 µl of 1 M HCl, then the products were further linearly amplified to demonstrate that the first primer extension products no longer contained a complete copy of the ribonucleotide containing primer used in the PCR reaction. The PCR products were primer extended using oligonucleotide Md114 which was labeled at its 5' end with $p^{32}$. Primer extension products made using PCR amplified fragment which had been treated with NaOH were shorter than primer extension products from PCR amplified fragments not cleaved with NaOH, depending on the primer used in the reaction. These results demonstrate that the incorporated ribonucleoside can be cleaved to prevent primer elongation in subsequent rounds of PCR amplification.

Use of Multiple (Nested) Primers

As explained above with references to FIGS. 5–6, when the LLA process of the inventions is initiated with a first set of primers, the second generation DNA molecules do not participate further in the primer extension reaction until, after a desired number of cycles, a second set of primers is added to the reaction. These second primers are able to utilize the second generation DNA molecules as template DNA because the second set of primers are 5' (with respect to the template) of the complementary site of the first set of primers. Following a desired number of cycles, a third set of primers can be added wherein the third primers are themselves 5' (with respect to the template) of the complementary site of the second set of primers.

But in addition to the sequential addition of new sets of primers, it is also possible according to the invention to simultaneously add all of the multiple sets of primers to the amplification reaction mixture. By this means, multiple (or nested) sets of primers containing non-replicable or cleavable elements can be simultaneously provided in a single amplification reaction mixture with the nucleic acid sequence to be amplified. The term "nested" is intended to refer to a series of two or more primers, typically as many as 14 to 18 primers, which are each complementary to portions of the nucleic acid strand to be amplified wherein those complementary portions are sequentially closer to the specific target nucleic acid sequence or gene of interest. In other words, each subsequent primer in the series is 5' (with respect to the template) of the complementary site of the next previous primer. This feature can be understood by reference to FIG. 14, where UP1-UP8 and LP2-LP11 represent the two sets of nested (multiple) primers which are each complementary to portions of the nucleic acid sequence of interest, but wherein the complementary portions are sequentially 5' from the end of the nucleic acid sequence to be amplified.

The multiple or nested primers may or may not overlap each other, so long as adjacent primers do not overlap at the point of the non-replicable or cleavable elements. This use of multiple, nested primers permits the amplification process to be conducted with all of the primers being simultaneously combined with the nucleic acid sequence of interest.

Example 8

LLA Using a Multiple (Nested) Set of Non-Replicable-Element-Containing Primers in a Single Amplification Reaction Mixture LLA primers containing the non-replicable propanediol element ("X") were synthesized. Primers flank the $\beta^S$ (20A>T) and $\beta^C$ (19G>A) mutation of the human β-globin gene (see FIG. 14). Primer sequences (5'->3') are as follows:

| UP 8 | TAAGCCAGTGCCAGAAGAGCCAAXGAC | SEQ ID NO:21 |
|------|------------------------------|--------------|
| UP 7 | TACGGCTGTCATCACTTAGACXTCA | SEQ ID NO:22 |
| UP 6 | CCCTGTGGAGCCACACCCTAGXGTT | SEQ ID NO:23 |
| UP 5 | AATCTACTCCCAGGAGCAGGGXGGG | SEQ ID NO:24 |
| UP 4 | GAGCCAGGGCTGGGCATAAAAXTCA | SEQ ID NO:25 |
| UP 3 | GGCAGAGCCATCTATTGCTTAXATT | SEQ ID NO:26 |
| UP 2 | TGCTTCTGACACAACTGTGTTXACT | SEQ ID NO:27 |
| UP 1 | AGCAACCTCAAACAGACACCAXGGT | SEQ ID NO:28 |
| LP 2 | CCTCACCACCAACTTCATCCAXGTT | SEQ ID NO:29 |
| LP 3 | AACCTTGATACCAACCTGCCCXGGG | SEQ ID NO:30 |

LLA reactions were performed using various combinations of nested LLA primers (10-primer set: UP 8, UP 7, UP 6, UP 5, UP 4, LP 4, LP 5, LP 6, LP 7, LP 8; 14-primer set: UP 8, UP 7, UP 6, UP 5, UP 4, UP 3, UP 2, LP 2, LP 3, LP 4, LP 5, LP 6, LP 7, LP 8; 18-primer set: UP 8, UP 7, UP 6, UP 5, UP 4, UP 3, UP 2, UP 1, LP 2, LP 3, LP 4, LP 5, LP 6, LP 7, LP 8, LP 9, LP 10, LP 11), different amounts of starting template DNA (ca. 200, 2000 and 20000 copies of human genomic DNA) and different cycle numbers (30, 35 and 40). The LLA reaction contained a set of LLA primers (each primer present at 10 pmoles), template DNA, 0.2 mM dNTPs, 10 mM Tris-HCl pH 9.2, 50 mM KCl, 2.5 mM $MgCl_2$, and 2 U AmpliTaq DNA polymerase (Perkin-Elmer) in a total volume of 50 µl. Reactions were placed in a thermal cycler (Perkin-Elmer 9600), heated at 94° C. for 1 minute, then subjected to 30, 35 or 40 cycles of heating and cooling as follows: 94° C., 30 seconds; 50° C., 1 minute; 72° C., 30 seconds.

To compare LLA and PCR efficiencies, PCRs were performed using the following primers (5'->3') corresponding to UP 8, LP 8 and LP 11 but without the non-replicable propanediol element "X":

| UP 8-x | TAAGCCAGTGCCAGAAGAGCCAAGGAC | SEQ ID NO:39 |
|--------|------------------------------|--------------|
| LP 8-x | GACCACCAGCAGCCTAAGGGTGGGA | SEQ ID NO:40 |
| LP 11-x | CAATCATTCGTCTGTTTCCCATTCT | SEQ ID NO:41 |

The PCR reaction contained 20 pmoles of UP 8-x, 20 pmoles of LP 8-x or LP 11-x, ca. 200, 2000 or 20,000 copies of template DNA, 0.2 mM dNTPs, 10 mM Tris-HCl pH 9.2, 50 mM KCl, 2.5 mM $MgCl_2$ and 2 U AmpliTaq DNA polymerase in a total volume of 50 µl. Reactions were placed in the thermal cycler, heated at 94° C. for 1 minute, then subjected to 30, 35 or 40 cycles of heating and cooling as follows: 94° C., 45 seconds; 62° C., 15 seconds; 72° C., 30 seconds. At the end of the last cycle, reactions were heated at 72° C. for 4.5 minutes.

Figure 14:
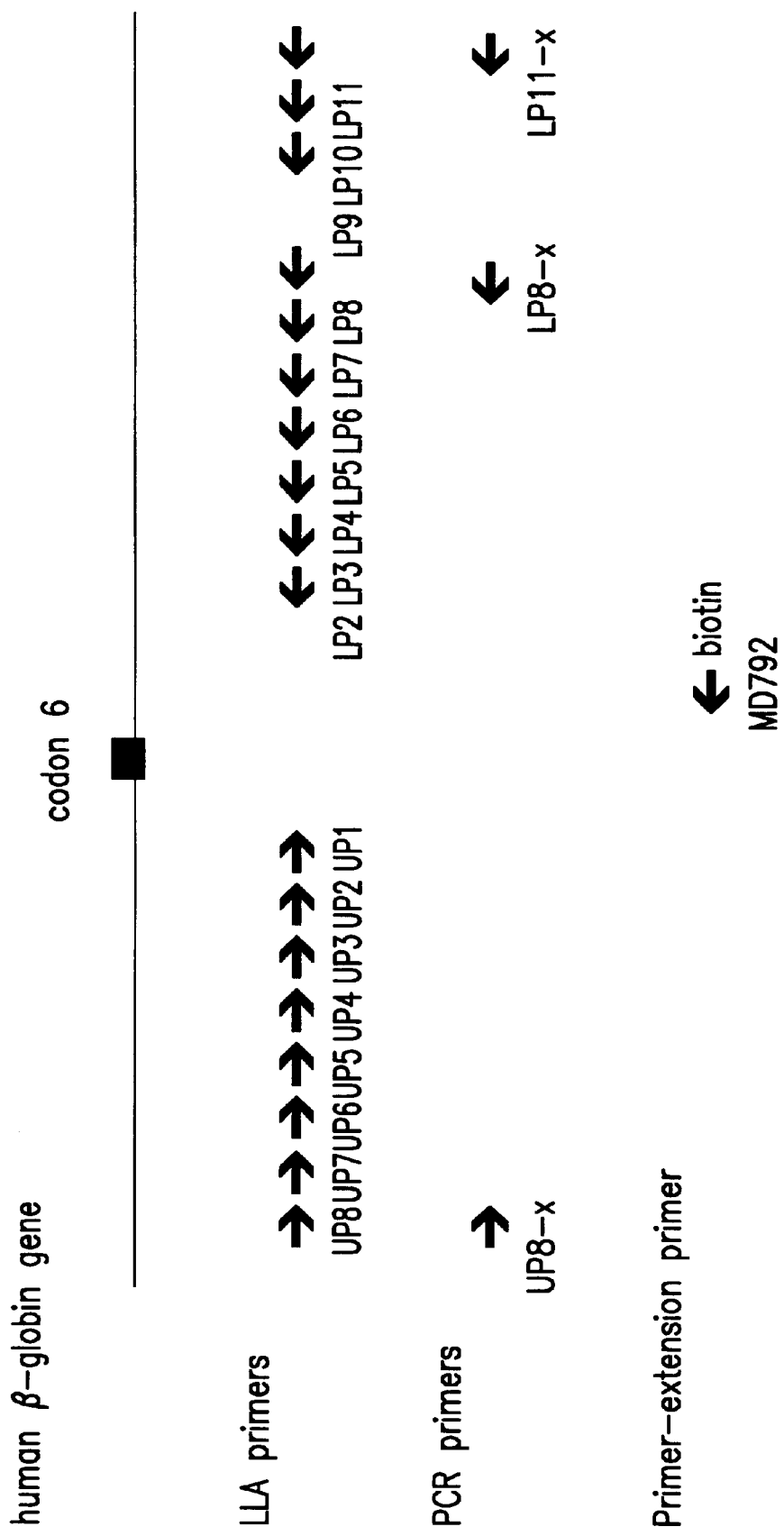
FIG. 14 is a schematic representation of the use of multiple or nested primers to amplify a specific sequence of interest, the human β-globin gene.

PCR and LLA amplification products were labeled in a primer extension reaction using the 5'-biotinylated primer MD 792 (5' CACCTTGCCCCACAGGGCAGTAACG 3' SEQ ID NO: 42; see FIG. 14). A 2 µl-aliquot of the LLA or PCR reaction was mixed with 18 µl of a mixture containing 10 pmoles MD 792, 10 mM Tris-HCl pH 9.2, 50 mM KCl, 2.5 mM MgCl$_2$, 0.2 mM dNTP's and 1 U AmpliTaq DNA polymerase. Reactions were placed in the thermal cycler and subjected to one cycle of heating and cooling as follows: 94° C. for 2 minutes, 55° C. for 2 minutes, 72° C. for 5 minutes.

Biotin-labeled DNA fragments were detected using the Bio-Rad mDx Variant Gene 1 kit, except that only the "conserved" microwell was used. The conserved well contains an immobilized oligonucleotide complementary to a region of the β-globin gene flanked by UP 1 and MD 792. There is an eighth base overlap between the conserved well capture oligonucleotide and MD 792; however, this short region of complementarity is not sufficient for MD 792 itself to be captured in the conserved well (data not shown). The primer extension reaction (20 μl) was mixed with 20 μl of denaturation solution then incubated for 10 minutes at room temperature. A 10 μl aliquot of the denatured primer extension product and 40 μl of hybridization solution were loaded into a conserved well. The well was incubated for one hr at 37° C. then washed five times with well wash buffer. Next, 50 μl of steptavidin-horseradish peroxidase conjugate were added to the well. The well was incubated for 30 min at 37° C. then washed five times with well wash buffer. Finally, 50 μl of tetramethyl benzidine were added to the well. After 10 minutes at room temperature, the calorimetric reaction was stopped by adding 50 μl of stop solution. Absorbance was read at 450 nm with 595 nm as reference.

Results

Figure 15A:
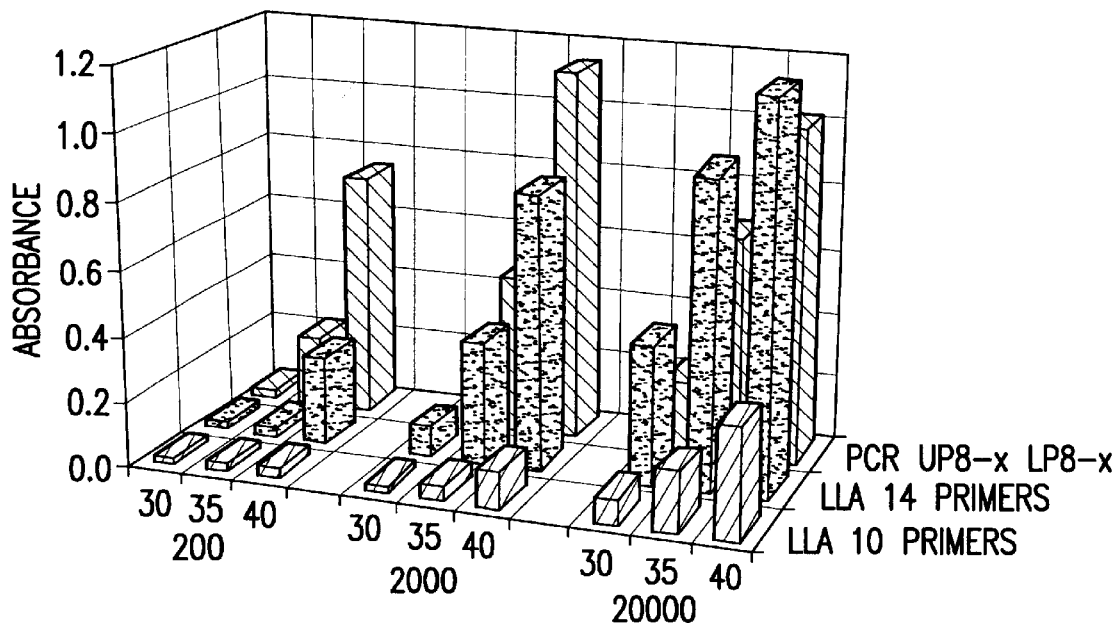
FIGS. 15A and B are bar graphs of the results of the amplification of a target sequence using 10, 14 or 18 nested primers in the LLA as compared to the standard PCR reaction.
Figure 15B:
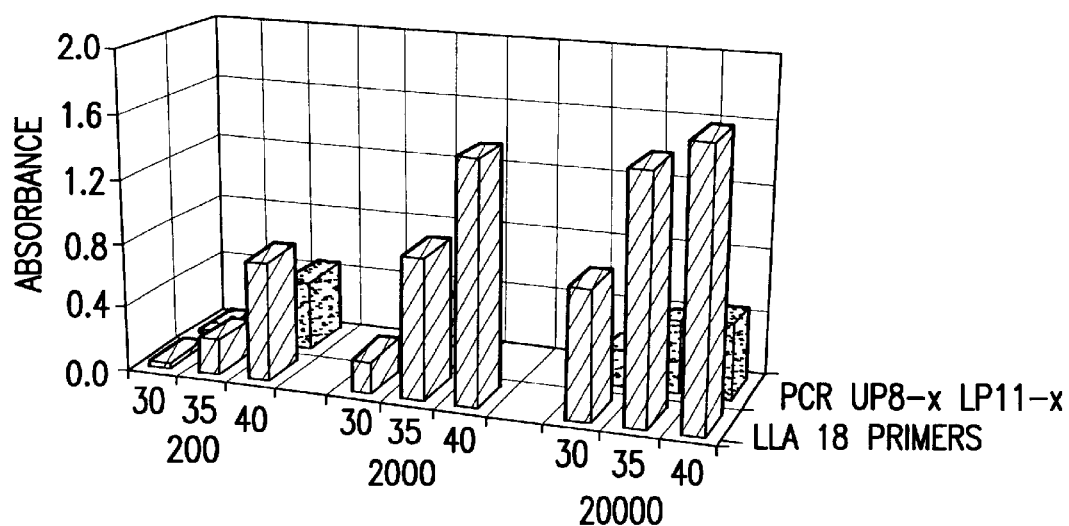

The use of a nested set of LLA primers, in which each primer contains a non-replicable element, resulted in the specific amplification of the target sequence as can be seen by the bar graph of the reaction in FIGS. 15A–B. The extent of amplification was dependent on the number of primers included in the reaction, the number of cycles and the starting amount of template DNA. When compared to the analogous PCR reaction (i.e., PCR using the non-propanediol-containing analogs of the two outermost LLA primers in, the set), the LLA reaction using 14 primers gave comparable amount of amplification (FIG. 15A) while the LLA reaction using 18 primers gave greater amplification (FIG. 15B).

Example 9

Resistance of LLA Amplification to Carry-Over Contamination Compared with PCR

From the preceding example, one LLA reaction (14-primer set, 20,000 copies of starting template, 40 amplification cycles) and one PCR reaction (primers UP 8-x and LP 8-x, 20,000 copies of starting template, 40 amplification cycles) gave approximately equal absorbance values after the primer extension step (1.184 and 1.019, respectively). The LLA reaction product was diluted serially ($10^{-3}$, $10^{-4}$, $10^{-5}$, $10^{-6}$, $10^{-7}$, $10^{-8}$, $10^{-9}$, $10^{-10}$, $10^{-11}$) then re-amplified in a "second round" LLA reaction containing 5 pmoles of each LLA primer (14-primer set), 0.2 mM dNTP's, 10 mM Tris-HCl pH 9.2, 50 mM KCl, 2.5 mM MgCl$_2$ and 1 U AmpliTaq DNA polymerase in a total volume of 25 μl. Reactions were placed in the thermal cycler, heated at 94° C. for 1 minute, then subjected to 40 cycles of heating and cooling as follows: 94° C., 30 seconds; 50° C. 1 minute; 72° C., 30 seconds.

Similar ten-fold serial dilutions of the PCR product were re-amplified in a second round PCR reaction containing 10 pmoles of UP 8-x, 10 pmoles of LP 8-x, 0.2 mM dNTP's, 10 mM Tris-HCl pH 9.2, 50 mM KCl, 2.5 mM MgCl$_2$ and 1 U AmpliTaq DNA polymerase in a total volume of 25 μl. Reactions were placed in the thermal cycler, heated to 94° C. for 1 minute, then subjected to 40 cycles of heating and cooling as follows: 94° C., 45 seconds; 62° C., 15 seconds; 72° C, 30 seconds. Reactions were then heated at 72° C. for 4.5 minutes.

To label the amplification products, a 2 μl-aliquot of the second round LLA or PCR reaction was mixed with 18 μl of a mixture containing 10 pmoles of 5'-biotinylated MD 792, 10 mM Tris-HCl pH 9.2, 50 mM KCl, 2.5 mM MgCl$_2$, 0.2 mM dNTP's and 1 U AmpliTaq DNA polymerase. Primer extension reactions were placed in the thermal cycler and subjected to one cycle of heating and cooling as follows: 94° C. for 2 minutes, 55° C. for 2 minutes, 72° C. for 5 minutes. The primer extension product was then detected using the "conserved" well of the Variant Gene 1 kit, as described above.

Results

Figure 16:
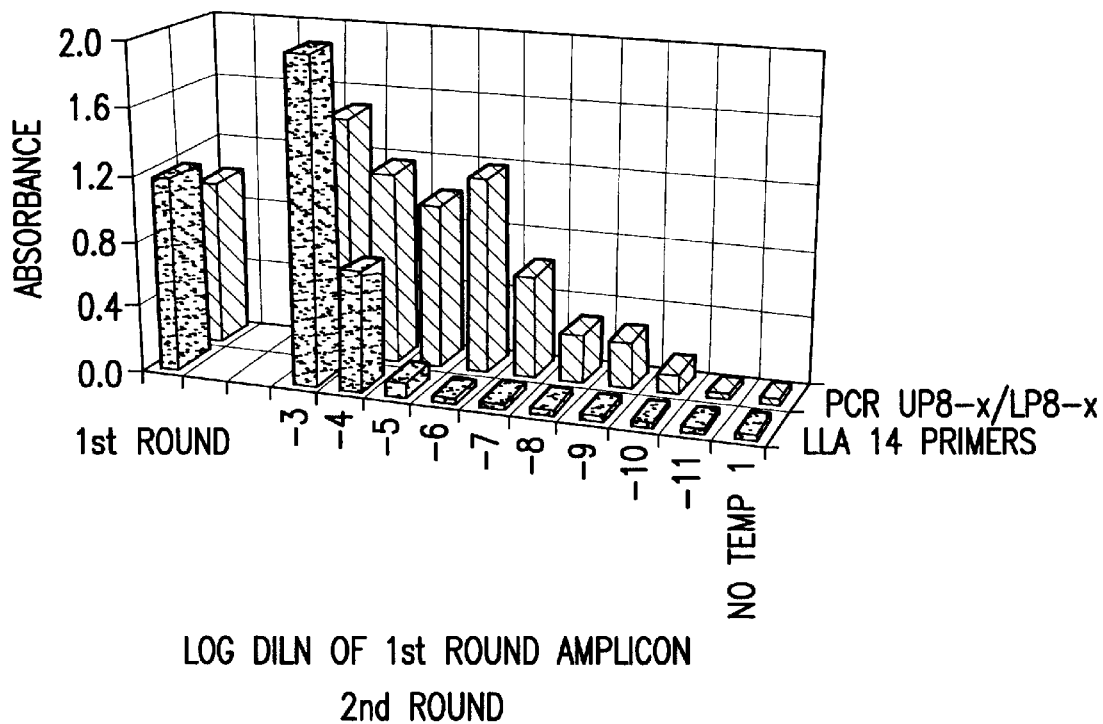
FIG. 16 is a bar graph of the results of the amplification of a target sequence using the LLA process as compared to the standard PCR reaction.

LLA was more resistant to carry-over contamination than PCR as can be seen from the bar graph of the results in FIG. 16. A $10^{-6}$ dilution of the first round LLA amplicon was sufficient to reduce second round amplification to background level. In the case of PCR, a $10^{-11}$ dilution was necessary to achieve this result.

Example 10

Multiplex Detection of the β-Globin S/C and the Factor V Leiden Mutations by LLA Eighteen Factor V gene specific primers, each containing the non-replicable propanediol element near the 3'-end, were synthesized. The primers flank the Factor V Leiden mutation (1691 G>A) site in exon 10. The 5' to 3' sequences are shown below:

| FVU9 | AGCACACCAACATGACACATGXATA | SEQ ID NO:43 |
|---|---|---|
| FVU8 | CACATGTACCCTAGAACTTAAAGXATA | SEQ ID NO:44 |
| FVU7 | AATTGGTTCCAGCGAAAGCXTAT | SEQ ID NO:45 |
| FVU6 | CAGGCAGGAACAACACCATXATC | SEQ ID NO:46 |
| FVU5 | AGAGCAGTTCAACCAGGGGXAAC | SEQ ID NO:47 |
| FVU4 | TCTTAGAGTTTGATGAACCCAXAGA | SEQ ID NO:48 |

LLA reactions were performed using the β-globin 18-primer set (UP 8, UP 7, UP 6, UP 5, UP 4, UP 3, UP 2, UP 1, LP 2, LP 3, LP 4, LP 5, LP 6, LP 7, LP 8, LP 9, LP 10, LP 11; see Example 8), and the Factor V 18-primer set. The primer sets were used singly (either the β-globin set alone or the Factor V set alone) or in combination (both the β-globin and Factor V primer sets together). The LLA reaction contained 10 pmoles of each primer, template DNA, 0.2 mM dNTPs, 10 mM Tris-HCl pH 9.2, 50 mM KCl, 2.5 mM MgCl$_2$, and 2 U AmpliTaq DNA polymerase (Perkin-Elmer) in a total volume of 50 μl. Reactions were placed in a thermal cycler (Perkin-Elmer 9600), heated at 94° C. for 2 minutes, then subjected to 35 cycles of heating and cooling as follows: 94° C., 45 seconds; 50° C., 30 seconds; 72° C., 30 seconds. Finally, the reactions were heated at 72° C. for 5 minutes.

To label the amplification products, a 4 μl-aliquot of the LLA reaction was mixed with 38 μl of a mixture containing 10 pmoles of 5'-biotinylated MD 792, 10 pmoles of 5'-biotinylated FVUO (5' CTACTTCTAATCTGTAAGAG-CAGA 3' SEQ ID NO: 61), 10 pmoles of biotinylated FVLO (5' GAAAGGTTACTTCAAGGACAAA 3' SEQ ID NO: 62), 10 mM Tris-HCl pH 9.2, 50 mM KCl, 2.5 mM MgCl$_2$, 0.2 mM dNTP's and 2 U AmpliTaq DNA polymerase. Primer extension reactions were placed in the thermal cycler and subjected to one cycle of heating and cooling as follows: 94° C. for 2 minutes, 60° C. for 2 minutes, 72° C. for 5 minutes.

The primer extension reaction (40 μl) was mixed with 40 μl of denaturation solution then incubated for 10 minutes at room temperature. A 10 μl aliquot of the denatured primer extension product and 40 μl of hybridization solution were loaded into each of four wells of the Variant Gene 1 kit. The first three wells contain immobilized oligonucleotides specific for the A, S, or C allele, while the fourth well contains an oligonucleotide that will hybridize to a conserved region of the β-globin gene. Similarly, a 10 μl aliquot of the denatured primer extension product and 40 μl of hybridization solution were loaded into each of two wells of the Factor V Leiden kit. In this case, the first well contains an oligonucleotide specific for the normal Factor V sequence, while the second well contains an oligonucleotide specific for the Factor V Leiden mutation. The wells were incubated for one hr at 37° C. then washed five times with well wash buffer.

Next, 50 μl of steptavidin-horseradish peroxidase conjugate were added to the well. The well was incubated for 30 min at 37° C. then washed five times with well wash buffer. Finally, 50 μl of tetramethyl benzidine were added to the well. After 10 minutes at room temperature, the calorimetric reaction was stopped by adding 50 μl of stop solution. Absorbance was read at 450 nm with 595 nm as reference.

Results. Raw absorbance readings ($A_{450-595}$) are shown on the following table:

example. In the concerted reaction, a 5'-biotin, propanediol-substituted oligonucleotide(s) is added together with the other LLA primers at the start of the thermal cycling. The 5'-biotin, propanediol-substituted oligonucleotide is complementary to a region of the gene flanked by the innermost non- biotinylated, propanediol-substituted primers.

The post-amplification and concerted methods of labeling were compared in the detection of the Factor V Leiden mutation. In the case of post-amplification labeling, the LLA reaction contained 10 pmoles of each primer in the Factor V 18 primer set, template DNA, 0.2 mM dNTPs, 10 mM Tris-HCl pH 9.2, 50 mM KCl, 2.5 mM $MgCl_2$, and 2 U AmpliTaq DNA polymerase (Perkin-Elmer) in a total volume of 50 μl. Reactions were placed in a thermal cycler (Perkin-Elmer 9600), heated at 94° C. for 2 minutes, then subjected to 35 cycles of heating and cooling as follows: 94° C., 45 seconds; 50° C., 30 seconds; 72° C., 30 seconds. Finally, the reactions were heated at 72° C. for 5 minutes. Amplification products were labeled by primer extension using 10 pmoles of 5'-biotinylated FVU0.1 (5' CTAATCT-GTAAGAGCAGATCCCXGGA 3' SEQ ID NO: 64) and 10 pmoles of 5'-biotinylated FVL0.1 (5' TTCTGAAAGGT-TACTTCAAGGAXAAA 3' SEQ ID NO: 64) as primers.

|  | Sample 1 | | | Sample 2 | | |
| --- | --- | --- | --- | --- | --- | --- |
|  | FV Primers | β-globin primers | FV + β-globin primers | FV Primers | β-globin primers | FV + β-globin primers |
| Factor V | | | | | | |
| Normal | 1.976 | 0.024 | 1.939 | 2.186 | 0.036 | 1.795 |
| Mutant | 0.048 | 0.042 | 0.047 | 0.040 | 0.056 | 0.036 |
| β-globin | | | | | | |
| A | 0.018 | 0.264 | 0.111 | 0.011 | 0.520 | 0.593 |
| S | 0.018 | 1.407 | 0.786 | 0.019 | 0.865 | 0.787 |
| C | 0.013 | 1.227 | 0.808 | 0.010 | 0.063 | 0.041 |
| conserved | 0.015 | 1.760 | 1.340 | 0.010 | 1.434 | 0.991 |

Multiplex LLA allowed the genotyping of samples with respect to the Factor V Leiden and β-globin S and C mutations. Thus, Sample 1 is Factor V Leiden normal/$\beta^S$/$\beta^C$ while Sample 2 is Factor V Leiden normal/$\beta^A$/$\beta^S$.

Example 11
The Use of Biotinylated, Non-Replicable Element-Containing Oligonucleotide Primers in Concerted LLA/Labeling Reactions In Examples 8–10, the LLA product was labeled post-amplification in a separate primer extension reaction using a 5'-biotinylated ofigonucleotide primer. The feasibility of a concerted reaction, in which the labeling of the amplification product occurs during the thermal cycling, is shown in this In the case of concerted amplification/labeling, the LLA reaction mixture used was the same as that for post-amplification labeling, except that 10 pmoles of 5'-biotinylated FVU0.1 and 10 pmoles of 5'-biotinylated FVL0.1 were also added. No post-amplification labeling was performed.

As a control, a reaction mixture containing 10 pmoles each of the 5'-biotinylated primers FVU0.1 and FVL0.1 but excluding the Factor V 18 primer set was used.

Amplification products from the concerted, post-amplification-labeled and control reactions were captured using Factor V Leiden normal and mutant specific microwells, and biotin detected as described in Example 10.

Results. Raw absorbance readings ($A_{450-595}$) are shown below:

|  | Sample 1 | | | Sample 2 | | |
| --- | --- | --- | --- | --- | --- | --- |
|  | Concerted amplification/ labeling | Post- amplification labeling | FVU0.1/ FVL0.1 only | Concerted amplification/ labeling | Post- amplification labeling | FVU0.1/ FVL0.1 only |
| Factor V | | | | | | |
| Normal | 2.081 | 1.738 | 0.014 | 1.958 | 1.786 | 0.020 |
| Mutant | 0.018 | 0.030 | 0.023 | 0.019 | 0.004 | 0.008 |

In this example, the presence of biotin tags in the two innermost LLA primers resulted in the synthesis of biotinylated amplification products which were then detected by streptavidin-enzyme conjugate chemistry.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A process for amplifying a nucleic acid sequence of interest contained within complementary first and second nucleic acid strands, comprising:

(a) combining the first and second strands in a reaction mixture with a series of nested primers, each primer containing a non-replicable element and/or a cleavable element, said series of nested primers comprising a plurality of primers which are complementary to different portions of said strands and are 5' to one another with respect to said strand and which do not overlap with one another at the position of said non-replicable element or cleavable element;

(b) subjecting said reaction mixture to conditions such that first generation primer extension products are produced from first primers, and not from other of said series of nested primers using the first and second strands as templates, wherein said first primers are primers of said nested primers which are most 3' with respect to said sequence of interest, and wherein the first primers are selected such that a first generation primer extension product from this step, when separated from its template, can serve as a template for synthesis of a second generation extension product of the first primer for the complement of said strand;

(c) separating the first generation primer extension products from their respective templates to produce single-stranded molecules;

(d) exposing said reaction mixture to conditions such that second generation primer extension products are generated by said first primers using first generation primer extension products as templates, wherein the second generation primer extension products contain at least a portion of the sequence of the nucleic acid sequence of interest and no more than an insufficient portion of the binding site for said first primers for producing said first generation primer extension products;

(e) separating the second generation primer extension products from their template to produce single stranded molecules;

(f) subjecting the reaction mixture of step (e) to reaction conditions such that next generation primer extension products are synthesized from another primer of said series of nested primers using second generation primer extension products as templates, and separating the thus produced next generation primer extension products from their templates to produce single-stranded molecules; and (g) repeating step (f) such that each repeat of the step comprises subjecting the reaction mixture to conditions such that next generation primer extension products are synthesized from a different primer of said series of nested primers using the next prior generation primer extension products as templates.

2. A process for amplifying a nucleic acid sequence of interest contained within complementary first and second nucleic acid strands, comprising:

(a) combining the first and second strands in a reaction mixture with a series of nested primes, each primer containing a non-replicable element and/or a cleavable element, said series of nested primers comprising a plurality of primers which are complementary to different portions of said strands and flank the sequence of interest but do not overlap with one another at the position of said non-replicable element or cleavable element;

(b) subjecting said reaction mixture to conditions whereby each of said primers is capable of binding to its respective complementary site;

(c) separating the first generation primer extension products from their respective templates to produce single-stranded molecules; and (d) repeating steps (b) and (c) whereby next generation primer extension products are synthesized from a different primer of said series of nested primers using the next prior generation primer extension products as templates.

3. A process according to claim 1 or 2, wherein the non-replicable element and/or cleavable element is not located at the terminal residue of any of said primers.

4. The process of claim 1 or 2, wherein the primer contains a non-replicable element.

5. The process of claim 1 or 2, wherein the primer contains a cleavable element.

6. The process of claim 4 wherein the cleavable element is a ribonucleoside.

7. A process according to claim 4 wherein the non-replicable element is a derivative of a deoxyribonucleotide.

8. A process according to claim 4 wherein the non-replicable element is a derivative of a ribonucleotide.

9. A process according to claim 7 wherein the non-replicable element is a residue of 1,3-propane diol.

10. A process according to claim 7 wherein the non-replicable element is a residue of 1,4-anhydro-2-deoxy-D-ribitol.

11. The process according to claim 1 or 2, wherein said complementary first and second nucleic acid strands are prepared from an RNA be reverse transcription.

* * * * *